US006465715B1

(12) United States Patent
Zwaal et al.

(10) Patent No.: US 6,465,715 B1
(45) Date of Patent: Oct. 15, 2002

(54) EXPRESSION OF DNA OR PROTEINS IN *C. ELEGANS*

(75) Inventors: Richard Zwaal; Wouter Asaert; Ingele Roelens; Thierry Bogaert, all of Ghent-Zwijnaarde (BE)

(73) Assignee: Devgen NV, Ghent-Zwijnaarde (BE)

( * ) Notice: Subject to any disclaimer, the term of this patent is extended or adjusted under 35 U.S.C. 154(b) by 0 days.

(21) Appl. No.: 09/526,993

(22) Filed: Mar. 16, 2000

(30) Foreign Application Priority Data

Mar. 16, 1999 (GB) ................................. 9906018

(51) Int. Cl.$^7$ ......................... G01N 33/00; A01K 67/00
(52) U.S. Cl. ............................................... 800/13; 800/3
(58) Field of Search ..................... 800/3, 13; 536/24.1, 536/24.31; 435/320.1, 325, 471

(56) References Cited

FOREIGN PATENT DOCUMENTS

WO    WO -98/28971    *    7/1998

OTHER PUBLICATIONS

J. E. Abrahnante et al., Dept. of Biochemistry, "Identification of heterochronic mutants in *caenorhabditis elegans*: temporal misexpression of a collagen::green fluorescent protein fusion gene," Genetics, Jul. 1998, 149:1335–1351.*
Young, J.M. and Hope, I.A., "Molecular Markers of Differentiation in *Caenorhabditis elegans* Obtained by Promoter Trapping", *Developmental Dynamics* 196:124–132 (1993).

Lambie, E.L. and Kimble, K., "Two homologous regulatory genes, lin–12 and glp–1, have overlapping functions", *Development* 112(1):231–240 (1991).
Broeks, et al., "A P–glycoprotein protects *Caenorhabditis elegans* against natural toxins", *EMBO Journal,* 14(9): 1858–1866 (1995).
International Search Report for PCT/EP00/02373, mailed Sep. 15, 2000.
The *C. elegans* Sequencing Consortium "Genome Sequence of the Namatode *C. elegans:* A Platform for Investigating Biology", *Science,* vol. 282, pp 2012–2018.
Oka, et al., "Three vha Genes Encode Proteolipids of *Caenorhabditis elegans* Vacuolar–type ATPase" *J. Biol. Chem.,* 272:39, pp 24387–24392 (1997).

* cited by examiner

*Primary Examiner*—Deborah Crouch
*Assistant Examiner*—Joseph Woitach
(74) *Attorney, Agent, or Firm*—Wolf, Greenfield and Sacks, P.C.

(57) ABSTRACT

DNA fragments from the promoter region of the *C. elegans* UL6 gene which are capable of functioning as promoters directing gene expression in the excretory cell of *C. elegans* are provided and also expression vectors and transgenic *C. elegans* containing these fragments. Also provided are screening methods performed in *C. elegans* for identifying compounds or mutations which have an affect on the morphology of the excretory canal. Compounds identified using these screening methods may have therapeutic potential in the treatment of a range of diseases for which the *C. elegans* excretory canal serves as a model.

13 Claims, 4 Drawing Sheets

UL6
6070 bp

SEQUENCE LISTING

<160> NUMBER OF SEQ ID NOS: 11

<210> SEQ ID NO 1
<211> LENGTH: 6070
<212> TYPE: DNA
<213> ORGANISM: Caenorhabditis Elegans

<400> SEQUENCE: 1

```
gatcgctcga ataaaaaatt ttataatgtc agattacgtt ttagatccaa aaaaaattag      60
gctgaatccg tttttgattc tctagaattt tgtttagcca aaaaacatcg cattgttctc     120
tctgtcgtta ttaaagtgcg caattaacaa atattcaaaa attcttattt aaaaaaccat     180
aggggggttcc ctaactattg cgaaattctc tttctctctc ggacattact atgagagatt    240
gaaccaattg aagagacgca gtgctaggaa gggaatgcgc cctggcgcca catatggtct     300
aagtctctct gaatcgtgtg ctctctacat tgggtcgact ctgcgagtgc ttttgagcgg     360
cgccgagacc gaaataagag agaaaacaga gggaaaaaag atagggaaca ttaattgatg     420
aaaaaagaaa cagatgacgt ggcaattctt ctttccggag ttttttttta ttggaagtgg     480
ggttattcaa gtaatgtagc aaaatgtatt taaatacatt tgtgacgtca caaatgtatt     540
taaatacatg tttttatata cttgaataag gttgtgacgt aatttttcta cactttttaa     600
ttttccgaca ctacttgaat aaccccaaaa gtgtacggtt tctttttttca aaacacgatt    660
gcaaccaaag gcgccggatt tttgaatttt tcaaaaatcg gaagatttaa aattttcgct     720
tttttatttt tattacttga taaaaattga attttatggt gaaatttcaa aatttgtttt     780
ggcttttcag ttgtccggaa aatcgaaaat gtttgttttt cgattcccac tgaaaaaatc     840
gaatttttc gatgaaacct ttgattgcaa tgttagaaaa atttctaaaa aattaacaag      900
aacactggaa caacacaaaa tcacaataat caacaccgga ccattggtac cgtataaaaa     960
gaaaaaaaaa tcgaattaat tgtaatagtt ctgaaaatct ttcataaata cccatttttga   1020
atataattat ttcttaataa atatataact tacagagaaa aaaatttcgg ggacgttaag    1080
gctcatagaa gaacacacga aaattaggta agttaaggct gaaggcattt ggcctactct    1140
acacgtagca gggaaatgat gtaaaatgga aaagagagaa aatatataaa acatatgaat    1200
gtgcaaggat tcggtatata aattatatat gaagggtcct tattaaggaa tttgttttcc    1260
tgtatgtaca atctagaaaa gagcagaagg gttattgaaa gggtggagta gagtcaaaat    1320
tgttttttta ctttaaatta cagaaaatgg acactaatga cggaatataa ctataaacat    1380
tttttctaaa ttttgaaaaa tgatttttttc aatttttgcac ctctcaaatt aagagcacta   1440
aagaaaatta cagaaaaacc agtaaaattt gagaatttga aacggatatc tccaaaaagt    1500
agtcgaagtc taagaatcaa aaaagaaatt aaaatttttt ttagttacgg tatatttttct   1560
```

-continued

```
gtcatttaaa gcagttgact ccactccacc tttaaaacaa tataaattat ctaatgaggc    1620
ctagcagaat atcggttcct caaatacgga ttataggtg tcatatcgcc ttttctccat     1680
tcgctccaaa cgattttggc gacaaccaga tgaaaagcga cgacgacaac aaaaacgaac    1740
acccagaatg ttgtcattcc tccagttgat tctccagatc gatgcatttc ataacttct     1800 tcttcgtgtg ccggtgctgc accaacttcc gacacgtgaa tggcatttct taggagttca    1860
agatgtcgtc gagatggagc aatgtagaga agagatgtta ctggtttcgt gacttttact    1920
ggtaattgaa ctggagtctt tccaagtgaa actgggctat cgaggcatcc accatcacaa    1980
acaaataatt gactagaaga tgaaacctga agaaatagt ttagagtatt ccaggataa      2040 atattttaa aatttaaata aaagacgtgt ttcagctctt ttgacaagga tttttattca     2100
ttttttgaga agtctcacta tgaaattcgg ggccagttca gtctatttaa gcaacaagaa    2160
accacaaact atgctacagt tgtaaaacat tctataaact attaccataa aataaggacg    2220
attttccgta tccaattta tatccactcg aatagtacca acaacaccca tattcgaata    2280
aactggaatt ccatgaaaat tcatttcacg atgcaaatca tgagcatcca atgctacttc    2340
caaatgagaa tcgtgataac tcgatgcagt caacgattga acaaatgctt gtgatgctcc    2400
aattgctcca gtgctcaaaa gattgttgca acctcgtttt tggaaagtga gcatccatgt    2460
attcacgagc tcaaaaagtt ttgtcggagt atcccagtct tgccacagac gtgatgggaa    2520
gagaagattt gaatgaccag tgtagcagag ctcgcttttc cgcgccaaat tttccagagg    2580
ctataaacat tctattttaa ttaggtaata atattcaatt acctttacag attccaaagt    2640
agccccatgc tcaattgttg gagcccgtaa attgctcatt aaaatgtatt ttgttgcatt    2700
aattctatct ccgtttaatg tatttggtgc tttcgaattc gcaacactga atcctgttaa    2760
atgcatcttg ctccatccgt caaaatgctc cgaatccaaa gttttcgagt cttttcctga    2820
ttggaaaaat cggatagcat cccgagaagc ttcttcactt gttggcttcg acgcaatcga    2880
gcatgtaaac cgaaatgact cttctctgaa ataaactgaa caaattaatt aattttttta    2940 atgtttttaaa taccttttt ctgtgaaact gaaacttttc caggtgcatc agtacaaaca    3000
acagcatacg atgctctagc aacttgccgc tgatgaaccg tcagctcgcc taattttgaa    3060
tgagcccacc agttggaact aagacgagac aagttgagtc ggaccgttga tttctgaaat    3120
taaatgttct ttttgtaatt ttaatgcatc aatttcaata aaattacagt tggattggaa    3180
acttgtatca attgaacaaa atagtttgga cgagttcgat gagcccatat ctgtgacgtc    3240
acacatgcac attcgccatc ctgaaacatt aatgtccaat aaatagttta ttatgtcgtg    3300
gctaaccatt gaaaaacatc gcagaatttt gaaaatgcca ttttgaaat ccgtcatttt     3360 tgtaacctca acaggttgtt gtccgtcaat ttcaatgttg agcccgggat aaaaattggt    3420
ttccacatcg agaactcggt ttttctcctg aactcgtaat tgtccgaatg aatcaacacc    3480
aatatatcca tttcccacaa actctacgct ttgattgtta attcctgtat cgaactccta    3540
aaaaaaagta aatatgaata attactaatt attcgactca catcaatctc tttttcccat    3600
aattttaact tttccgctga acattgatgc tgttttgtga atgatgtgcc ggaagacgtt    3660
cctcgcgaga agatgaaaat gacgaataaa acaactccaa taattatcgc taatcttcgt    3720
tttggatatc gtcgaaccat acgcatttta ctttcgaaat ccatattttc tattcgacgc    3780
acgaaagtgc gccacgttat tgcggcgctc attttggagg ggaaatccgc ctgaaaaatc    3840
aattgtttgt attgtgaaat ttcgaagagg cataaaacaa gaaaacggac atgaaagcgc    3900
gttgcatgca aggttagttg cctgtttaag cattatcccc gcatgtagct tgttcggcac    3960
```

```
cgttaaaaat gctgagtaat cagcttttta gaatttaaaa tattaaactt ttaaaattgc     4020
aacaaacatc gacaaatatt caagaggcga atgatatcgg gaatttcgat tgaaacgaaa     4080
ctgttttgaa attcaaaaag tattttcaaa gtattgtccg caaggcacat cacgcaaact     4140
tgcagaatct accgtatccc atacatttt atagttttc cctcagtttt taaaattaaa      4200
aacgctgaaa aagcgattaa atttatttaa atgcatcgtt cgaataaaat aaagtttatc    4260
ttttgataaa aacatgagtt tcctttggag aaaagtaggg atttcgcctt tcaaaaaatt    4320
atttcgtgca ggatgctatt ttcgtggcga aacccatact caagagctca tgcgtcttct    4380
tgattactgt agatgtttgg caacttattt ttacataaaa acgttttcat tcattatttc    4440
catcattcat ttatctttct gtgtttttag ttagttttag ctagtttttt tctaaattcc    4500
taactttaaa aaatctggaa aagaaaatta aaaaattttg tccctattat ttattttatt    4560
actggaaaat cttcaaacag gaaaacccac gcgttttgc ttattgctgt atttatgaaa     4620
aaaaaaacaa tcaatattgg tcaagtaaat aagaaaaaat taacgaatct ctatctgaca    4680
ccagatgcga ccctctattc cacttctctg ttcatctgct gcttcttttg tttaaccaga    4740
taaatctccc tcggggaaaa ccgtcaaaaa aaggcaaact aaatgcaaac acgctctata    4800
gacaaaatgt gtttggtctc gtcacgaatg gtgagagaga attggcctcc gccgcagaga    4860
tcgcttgatt attggcctcc agtgggcaat gtcgggaaa accaaactat tgatgagagg     4920
tatcgacgaa aaatcaacaa tgaccaactt tttgttacag ttttgttata aatatgagtt    4980
ttggatattc cattgcgtat ttttcttttc tactttcaaa aaatctgctc caacctttaa    5040
tggcttttcc tgtcttgtca aaatctggat ttttgaatat ataatttta aaaccatcaa     5100 attcagcgaa atgaaatcat gtaatacaat tttttatttt ttccgactgt tgtgtattcc    5160
atcaaactat tcaaaaaatc aatataatga ttttttttc atttttcgcg attttttatt    5220
attttgtcgt ctgaaaacct ttttactaat aaaataattt acagggaaaa ccactaacga    5280
ctgtagccat gggaatcagc gacaacgacg ttcagaagca gctccgccac atgatggctt    5340
tcattgagca agaggccaat gagaaggctg aggagatcga tgctaaagcc gaggaagaat    5400
tcaacattga gaaagtaagg aattaaaaca tttactcctt taaaactata ctaaaatctc    5460
ttctaaaaaa cggaaaacct tgaaattatg aattcattca aattgtttca gggacgtctt    5520
gttcaacaac aacgtcaaaa gattatggaa ttcttcgaga agaaggagaa acaagtcgag    5580
cttcaacgca aaattcaagc ctccaactct ctcaacgctg gacgtcttcg ttgcttgaag    5640
gtgagagaaa acgtttctca acattttcaa aaacattaat cgccttaaaa ttgaaaacca    5700
gttctgaatc ggacacattt gaattaaaaa catattttca ggctcgtgaa gaccacatcg    5760
gagccgtact cgacgaggct cgctcgaatc tctcccgtat ttccggagat gctgctcgtt    5820
atccagctat tttgaaggga cttgtcatgc aaggacttct tcaattgctc gaaaggaag    5880 tcgtccttcg ttgccgtgag aaggatcttc gtcttgttga gcaacttttg ccagagtgcc    5940
ttgacggact tcaaaggag tggggaagca ccaccaaggt cgttctcgat aaacaaaact    6000
tcttgccatc ggagtctgct ggaggagttg aactttctgc tcgtgctgga aagatccccg    6060
ggattggcca                                                            6070
```

<210> SEQ ID NO 2
<211> LENGTH: 3224
<212> TYPE: DNA
<213> ORGANISM: Caenorhabditis Elegans

```
<400> SEQUENCE: 2
aagcttcttc acttgttggc ttcgacgcaa tcgagcatgt aaaccgaaat gactcttctc      60
tgaaataaac tgaacaaatt aattaatttt tttaatgttt taaatatacc ttttctgtga     120
aactgaaact tttccaggtg catcagtaca acaacagca tacgatgctc tagcaacttg     180
ccgctgatga accgtcagct cgcctaattt tgaatgagcc caccagttgg aactaagacg     240
agacaagttg agtcggaccg ttgatttctg aaattaaatg ttcttttttgt aattttaatg     300
catcaatttc aataaaatta cagttggatt ggaaacttgt atcaattgaa caaaatagtt     360
tggacgagtt cgatgagccc atatctgtga cgtcacacat gcacattcgc catcctgaaa     420
cattaatgtc caataaatag tttattatgt cgtggctaac cattgaaaaa catcgcagaa     480
ttttgaaaat gccattttttg aaatccgtca tttttgtaac ctcaacaggt tgttgtccgt     540
caatttcaat gttgagcccg ggataaaaat tggtttccac atcgagaact cggttttttct     600
cctgaactcg taattgtccg aatgaatcaa caccaatata tccatttccc acaaactcta     660
cgctttgatt gttaattcct gtatcgaact cctaaaaaaa agtaaatatg aataattact     720
aattattcga ctcacatcaa tctcttttttc ccataatttt aacttttccg ctgaacattg     780
atgctgttttt gtgaatgatg tgccggaaga cgttcctcgc gagaagatga aaatgacgaa     840
taaaacaact ccaataatta tcgctaatct tcgttttgga tatcgtcgaa ccatacgcat     900
tttactttcg aaatccatat tttctattcg acgcacgaaa gtgcgccacg ttattgcggc     960
gctcattttg gagggaaat ccgcctgaaa atcaattgt ttgtattgtg aaatttcgaa    1020
gaggcataaa acaagaaaac ggacatgaaa gcgcgttgca tgcaaggtta gttgcctgtt    1080
taagcattat ccccgcatgt agcttgttcg gcaccgttaa aaatgctgag taatcagctt    1140
tttagaattt aaaatattaa acttttaaaa ttgcaacaaa catcgacaaa tattcaagag    1200
gcgaatgata tcgggaattt cgattgaaac gaaactgttt tgaaattcaa aaagtatttt    1260
caaagtattg tccgcaaggc acatcacgca aacttgcaga atctaccgta tcccatacat    1320
ttttatagtt tttccctcag tttttaaaat taaaaacgct gaaaagcga ttaaatttat    1380
ttaaatgcat cgttcgaata aaataaagtt tatcttttga taaaaacatg agtttccttt    1440
ggagaaaagt agggatttcg cctttcaaaa aattatttcg tgcaggatgc tatttttcgtg    1500
gcgaaaccca tactcaagag ctcatgcgtc ttcttgatta ctgtagatgt ttggcaactt    1560
attttttacat aaaaacgttt tcattcatta tttccatcat tcatttatct ttctgtgttt    1620
ttagttagtt ttagctagtt ttttttctaaa ttcctaactt taaaaaatct ggaaaagaaa    1680
attaaaaaat tttgtcccta ttatttattt tattactgga aaatcttcaa acaggaaaac    1740
ccaccgcgtt ttgcttattg ctgtatttat gaaaaaaaaa acaatcaata ttggtcaagt    1800
aaataagaaa aaattaacga atctctatct gacaccagat gcgaccctct attccacttc    1860
tctgttcatc tgctgcttct tttgtttaac cagataaatc tccctcgggg aaaaccgtca    1920
aaaaaggca aactaaatgc aaacacgctc tatagacaaa atgtgttttgg tctcgtcacg    1980
aatggtgaga gagaattggc ctccgccgca gagatcgctt gattattggc ctccagtggg    2040
caatgtcggg gaaaccaaa ctattgatga gaggtatcga cgaaaaatca acaatgacca    2100
acttttttgtt acagttttgt tataaatatg agttttggat attccattgc gtattttttct    2160
tttctacttt caaaaaatct gctccaacct ttaatggctt ttcctgtctt gtcaaaatct    2220
ggattttttga atatataatt tttaaaacca tcaaattcag cgaaatgaaa tcatgtaata    2280
caattttttta tttttttccga ctgttgtgta ttccatcaaa ctattcaaaa aatcaatata    2340
```

-continued

```
atgattttt tttcatttt cgcgatttt tattatttg tcgtctgaaa accttttac    2400 taataaaata atttacaggg aaaaccacta acgactgtag ccatgggaat cagcgacaac    2460
gacgttcaga agcagctccg ccacatgatg gctttcattg agcaagaggc caatgagaag    2520
gctgaggaga tcgatgctaa agccgaggaa gaattcaaca ttgagaaagt aaggaattaa    2580
aacatttact cctttaaaac tatactaaaa tctcttctaa aaaacggaaa accttgaaat    2640
tatgaattca ttcaaattgt ttcagggacg tcttgttcaa caacaacgtc aaagattat    2700 ggaattcttc gagaagaagg agaaacaagt cgagcttcaa cgcaaaattc aagcctccaa    2760
ctctctcaac gctggacgtc ttcgttgctt gaaggtgaga gaaacgtttt ctcaacattt    2820
tcaaaaacat taatcgcctt aaaattgaaa accagttctg aatcggacac atttgaatta    2880
aaaacatatt ttcaggctcg tgaagaccac atcggagccg tactcgacga ggctcgctcg    2940
aatctctccc gtatttccgg agatgctgct cgttatccag ctattttgaa gggacttgtc    3000
atgcaaggac ttcttcaatt gctcgaaaag gaagtcgtcc ttcgttgccg tgagaaggat    3060
cttcgtcttg ttgagcaact tttgccagag tgccttgacg gacttcaaaa ggagtgggga    3120
agcaccacca aggtcgttct cgataaacaa aacttcttgc catcggagtc tgctggagga    3180
gttgaacttt ctgctcgtgc tggaaagatc cccgggattg gcca                     3224
```

<210> SEQ ID NO 3
<211> LENGTH: 2167
<212> TYPE: DNA
<213> ORGANISM: Caenorhabditis Elegans

<400> SEQUENCE: 3

```
gcatgcaagg ttagttgcct gtttaagcat tatccccgca tgtagcttgt tcggcaccgt      60
taaaaatgct gagtaatcag ctttttagaa tttaaaatat taaactttta aaattgcaac    120
aaacatcgac aaatattcaa gaggcgaatg atatcgggaa tttcgattga aacgaaactg    180
ttttgaaatt caaaaagtat tttcaaagta ttgtccgcaa ggcacatcac gcaaacttgc    240
agaatctacc gtatcccata cattttttata gttttttccct cagttttttaa aattaaaaac    300 gctgaaaaag cgattaaatt tatttaaatg catcgttcga ataaaataaa gtttatcttt    360
tgataaaaac atgagtttcc tttggagaaa agtagggatt tcgcctttca aaaaattatt    420
tcgtgcagga tgctattttc gtggcgaaac ccatactcaa gagctcatgc gtcttcttga    480
ttactgtaga tgtttggcaa cttatttta cataaaaacg ttttcattca ttatttccat    540
cattcattta tctttctgtg tttttagtta gtttagcta gttttttct aaattcctaa    600 ctttaaaaaa tctggaaaag aaaattaaaa aattttgtcc ctattattta ttttattact    660
ggaaaatctt caaacaggaa aacccaccgc gtttgctta ttgctgtatt tatgaaaaaa    720
aaaacaatca atattggtca agtaaataag aaaaaattaa cgaatctcta tctgacacca    780
gatgcgaccc tctattccac ttctctgttc atctgctgct tctttttgttt aaccagataa    840 atctccctcg gggaaaaccg tcaaaaaaag gcaaactaaa tgcaaacacg ctctatagac    900
aaaatgtgtt tggtctcgtc acgaatggtg agagagaatt ggcctccgcc gcagagatcg    960
cttgattatt ggcctccagt gggcaatgtc ggggaaaacc aaactattga tgagaggtat    1020
cgacgaaaaa tcaacaatga ccaactttt gttacagttt tgttataaat atgagttttg    1080
gatattccat tgcgtatttt tcttttctac tttcaaaaaa tctgctccaa cctttaatgg    1140
cttttcctgt cttgtcaaaa tctggatttt tgaatatata atttttaaaa ccatcaaatt    1200
```

-continued

```
cagcgaaatg aaatcatgta atacaatttt ttatttttc cgactgttgt gtattccatc   1260
aaactattca aaaatcaat ataatgattt tttttcatt tttcgcgatt tttattatt    1320
ttgtcgtctg aaaacctttt tactaataaa ataatttaca gggaaaacca ctaacgactg  1380
tagccatggg aatcagcgac aacgacgttc agaagcagct ccgccacatg atggctttca  1440
ttgagcaaga ggccaatgag aaggctgagg agatcgatgc taaagccgag gaagaattca  1500
acattgagaa agtaaggaat taaaacattt actcctttaa aactatacta aaatctcttc  1560
taaaaaacgg aaaaccttga aattatgaat tcattcaaat tgtttcaggg acgtcttgtt  1620
caacaacaac gtcaaaagat tatggaattc ttcgagaaga aggagaaaca agtcgagctt  1680
caacgcaaaa ttcaagcctc caactctctc aacgctggac gtcttcgttg cttgaaggtg  1740
agagaaaacg tttctcaaca ttttcaaaaa cattaatcgc cttaaaattg aaaaccagtt  1800
ctgaatcgga cacatttgaa ttaaaaacat attttcaggc tcgtgaagac cacatcggag  1860
ccgtactcga cgaggctcgc tcgaatctct cccgtatttc cggagatgct gctcgttatc  1920
cagctatttt gaagggactt gtcatgcaag gacttcttca attgctcgaa aaggaagtcg  1980
tccttcgttg ccgtgagaag gatcttcgtc ttgttgagca acttttgcca gagtgccttg  2040
acggacttca aaaggagtgg ggaagcacca ccaaggtcgt tctcgataaa caaaacttct  2100
tgccatcgga gtctgctgga ggagttgaac tttctgctcg tgctggaaag atccccggga  2160
ttggcca                                                            2167
```

<210> SEQ ID NO 4
<211> LENGTH: 1308
<212> TYPE: DNA
<213> ORGANISM: Caenorhabditis Elegans

<400> SEQUENCE: 4

```
gcatgcaagg ttagttgcct gtttaagcat tatccccgca tgtagcttgt tcggcaccgt    60
taaaaatgct gagtaatcag cttttttagaa tttaaaatat taaactttta aaattgcaac  120
aaacatcgac aaatattcaa gaggcgaatg atatcgggaa tttcgattga aacgaaactg  180
ttttgaaatt caaaaagtat tttcaaagta ttgtccgcaa ggcacatcac gcaaacttgc  240
agaatctacc gtatcccata cattttttata gttttttccct cagttttttaa aattaaaaac  300
gctgaaaaag cgattaaatt tatttaaatg catcgttcga ataaaataaa gtttatctttt  360
tgataaaaac atgagtttcc tttggagaaa agtagggatt tcgcctttca aaaaattatt  420
tcgtgcagga tgctatttttc gtggcgaaac ccatactcaa gagctcatgc gtcttcttga  480
ttactgtaga gtgtttggcaa cttatttttta cataaaaacg ttttcattca ttatttccat  540
cattcattta tctttctgtg tttttagtta gttttagcta gttttttttct aaattcctaa  600
ctttaaaaaa tctggaaaag aaaattaaaa aattttgtcc ctattattta ttttattact  660
ggaaaatctt caaacaggaa aacccaccgc gttttgctta ttgctgtatt tatgaaaaaa  720
aaacaatca atattggtca agtaaataag aaaaaattaa cgaatctcta tctgacacca  780
gatgcgaccc tctattccac ttctctgttc atctgctgct tcttttgttt aaccagataa  840
atctccctcg gggaaaaccg tcaaaaaaag gcaaactaaa tgcaaacacg ctctatagac  900
aaaatgtgtt tggtctcgtc acgaatggtg agagagaatt ggcctccgcc gcagagatcg  960
cttgattatt ggcctccagt gggcaatgtc ggggaaaacc aaactattga tgagaggtat 1020
cgacgaaaaa tcaacaatga ccaacttttt gttacagttt tgttataaat atgagttttg 1080
gatattccat tgcgtatttt tcttttctac tttcaaaaaa tctgctccaa cctttaatgg 1140
```

-continued

| cttttcctgt cttgtcaaaa tctggatttt tgaatatata atttttaaaa ccatcaaatt | 1200 |
| cagcgaaatg aaatcatgta atacaatttt ttatttttc cgactgttgt gtattccatc | 1260 |
| aaactattca aaaatcaat ataatgattt tttttcatt tttcgcga | 1308 |

<210> SEQ ID NO 5
<211> LENGTH: 1707
<212> TYPE: DNA
<213> ORGANISM: Caenorhabditis Elegans

<400> SEQUENCE: 5

| gagctcatgc gtcttcttga ttactgtaga tgtttggcaa cttatttta cataaaacg | 60 |
| ttttcattca ttatttccat cattcattta tctttctgtg ttttagtta gttttagcta | 120 |
| gtttttttct aaattcctaa ctttaaaaaa tctggaaaag aaaattaaaa aattttgtcc | 180 |
| ctattattta ttttattact ggaaaatctt caaacaggaa aacccaccgc gttttgctta | 240 |
| ttgctgtatt tatgaaaaaa aaaacaatca atattggtca agtaaataag aaaaaattaa | 300 |
| cgaatctcta tctgacacca gatgcgaccc tctattccac ttctctgttc atctgctgct | 360 |
| tcttttgttt aaccagataa atctccctcg gggaaaaccg tcaaaaaag gcaaactaaa | 420 |
| tgcaaacacg ctctatagac aaaatgtgtt tggtctcgtc acgaatggtg agagagaatt | 480 |
| ggcctccgcc gcagagatcg cttgattatt ggcctccagt gggcaatgtc ggggaaaacc | 540 |
| aaactattga tgagaggtat cgacgaaaaa tcaacaatga ccaactttt gttacagttt | 600 |
| tgttataaat atgagttttg gatattccat tgcgtatttt tcttttctac tttcaaaaaa | 660 |
| tctgctccaa cctttaatgg cttttcctgt cttgtcaaaa tctggatttt tgaatatata | 720 |
| atttttaaaa ccatcaaatt cagcgaaatg aaatcatgta atacaatttt ttatttttc | 780 |
| cgactgttgt gtattccatc aaactattca aaaatcaat ataatgattt tttttcatt | 840 |
| tttcgcgatt ttttattatt ttgtcgtctg aaaaccttt tactaataaa ataatttaca | 900 |
| gggaaaacca ctaacgactg tagccatggg aatcagcgac aacgacgttc agaagcagct | 960 |
| ccgccacatg atggctttca ttgagcaaga ggccaatgag aaggctgagg agatcgatgc | 1020 |
| taaagccgag gaagaattca acattgagaa agtaaggaat taaaacattt actcctttaa | 1080 |
| aactatacta aaatctcttc taaaaaacgg aaaaccttga aattatgaat tcattcaaat | 1140 |
| tgtttcaggg acgtcttgtt caacaacaac gtcaaaagat tatggaattc ttcgagaaga | 1200 |
| aggagaaaca agtcgagctt caacgcaaaa ttcaagcctc caactctctc aacgctggac | 1260 |
| gtcttcgttg cttgaaggtg agagaaaacg tttctcaaca ttttcaaaaa cattaatcgc | 1320 |
| cttaaaattg aaaaccagtt ctgaatcgga cacatttgaa ttaaaaacat attttcaggc | 1380 |
| tcgtgaagac cacatcggag ccgtactcga cgaggctcgc tcgaatctct cccgtatttc | 1440 |
| cggagatgct gctcgttatc cagctatttt gaagggactt gtcatgcaag gacttcttca | 1500 |
| attgctcgaa aaggaagtcg tccttcgttg ccgtgagaag gatcttcgtc ttgttgagca | 1560 |
| acttttgcca gagtgccttg acggacttca aaaggagtgg ggaagcacca ccaaggtcgt | 1620 |
| tctcgataaa caaaacttct tgccatcgga gtctgctgga ggagttgaac tttctgctcg | 1680 |
| tgctggaaag atccccggga ttggcca | 1707 |

<210> SEQ ID NO 6
<211> LENGTH: 789
<212> TYPE: DNA
<213> ORGANISM: Caenorhabditis Elegans -continued

```
<400> SEQUENCE: 6
ttttcattca ttatttccat cattcattta tctttctgtg ttttagtta gttttagcta      60
gtttttttct aaattcctaa ctttaaaaaa tctggaaaag aaaattaaaa aattttgtcc     120
ctattattta ttttattact ggaaaatctt caaacaggaa acccaccgc gttttgctta     180
ttgctgtatt tatgaaaaaa aaacaatca atattggtca agtaaataag aaaaaattaa     240
cgaatctcta tctgacacca gatgcgaccc tctattccac ttctctgttc atctgctgct    300
tcttttgttt aaccagataa atctccctcg gggaaaaccg tcaaaaaaag gcaaactaaa    360
tgcaaacacg ctctatagac aaaatgtgtt tggtctcgtc acgaatggtg agagagaatt    420
ggcctccgcc gcagagatcg cttgattatt ggcctccagt gggcaatgtc ggggaaaacc    480
aaactattga tgagaggtat cgacgaaaaa tcaacaatga ccaactttttt gttacagttt    540
tgttataaat atgagttttg gatattccat tgcgtatttt tcttttctac tttcaaaaaa    600
tctgctccaa cctttaatgg cttttcctgt cttgtcaaaa tctggatttt tgaatatata    660
atttttaaaa ccatcaaatt cagcgaaatg aaatcatgta atacaatttt ttattttttc    720
cgactgttgt gtattccatc aaactattca aaaaatcaat ataatgattt tttttcatt    780
tttcgcgat                                                              789

<210> SEQ ID NO 7
<211> LENGTH: 397
<212> TYPE: DNA
<213> ORGANISM: Caenorhabditis Elegans

<400> SEQUENCE: 7
ggtctcgtca cgaatggtga gagagaattg gcctccgccg cagagatcgc ttgattattg     60
gcctccagtg ggcaatgtcg gggaaaacca aactattgat gagaggtatc gacgaaaaat    120
caacaatgac caactttttg ttacagtttt gttataaata tgagttttgg atattccatt    180
gcgtattttt cttttctact ttcaaaaaat ctgctccaac ctttaatggc ttttcctgtc    240
ttgtcaaaat ctggattttt gaatatataa ttttaaaac catcaaattc agcgaaatga    300
aatcatgtaa tacaattttt tatttttttcc gactgttgtg tattccatca aactattcaa    360
aaaatcaata taatgatttt ttttcattt ttcgcga                               397

<210> SEQ ID NO 8
<211> LENGTH: 6202
<212> TYPE: DNA
<213> ORGANISM: Artificial Sequence
<220> FEATURE:
<223> OTHER INFORMATION: plasmid pGF2006

<400> SEQUENCE: 8
agcttgcatg caaggttagt tgcctgttta agcattatcc ccgcatgtag cttgttcggc      60
accgttaaaa atgctgagta atcagctttt tagaatttaa aatattaaac ttttaaaatt    120
gcaacaaaca tcgacaaata ttcaagaggc gaatgatatc gggaatttcg attgaaacga    180
aactgttttg aaattcaaaa agtattttca agtattgtc cgcaaggcac atcacgcaaa    240
cttgcagaat ctaccgtatc ccatacattt ttatagtttt tccctcagtt tttaaaatta    300
aaacgctga aaaagcgatt aaatttattt aaatgcatcg ttcgaataaa ataaagttta    360
tcttttgata aaaacatgag tttccttttgg agaaagtag ggatttcgcc tttcaaaaaa    420
ttatttcgtg caggatgcta ttttcgtggc gaaacccata ctcaagagct catgcgtctt    480
cttgattact gtagatgttt ggcaacttat ttttacataa aaacgttttc attcattatt    540
```

-continued

```
tccatcattc atttatcttt ctgtgttttt agttagtttt agctagtttt tttctaaatt    600
cctaacttta aaaatctgg aaagaaaat taaaaaattt tgtccctatt atttatttta    660
ttactggaaa atcttcaaac aggaaaaccc accgcgtttt gcttattgct gtatttatga    720
aaaaaaaac aatcaatatt ggtcaagtaa ataagaaaaa attaacgaat ctctatctga    780
caccagatgc gaccctctat tccacttctc tgttcatctg ctgcttcttt tgtttaacca    840
gataaatctc cctcggggaa aaccgtcaaa aaaaggcaaa ctaaatgcaa acacgctcta    900
tagacaaaat gtgtttggtc tcgtcacgaa tggtgagaga gaattggcct ccgccgcaga    960
gatcgcttga ttattggcct ccagtgggca atgtcgggga aaccaaaact attgatgaga   1020
ggtatcgacg aaaaatcaac aatgaccaac ttttgttac agttttgtta taaatatgag   1080
ttttggatat tccattgcgt attttctttt tctactttca aaaatctgc tccaaccttt   1140
aatggctttt cctgtcttgt caaaatctgg attttgaat atataatttt taaaaccatc   1200
aaattcagcg aaatgaaatc atgtaataca atttttatt tttccgact gttgtgtatt   1260
ccatcaaact attcaaaaaa tcaatataat gattttttt tcattttcg gactctagag   1320
gatccccggg gattggccaa aggacccaaa ggtatgtttc gaatgatact aacataacat   1380
agaacatttt caggaggacc cttgcttggc tagcaaaaat gcataaggtt ttgctggcac   1440
tgttctttat ctttctggca ccagcatccg cactggcagt ctccgaaccg gcctgcagga   1500
tcgattttt gcaaattacg agcgttgtag ggggcggacg ataggtccta taggttttgt   1560
atatcatcat tcattcattc attggtacat tcatttaccc accttcctct ttctgagctt   1620
ctctggagtt ctgtgcttcc ttttcccctt atctttatac tgtaattttt aactttcagg   1680
cattgattgg atccccggga ttggccaaag gacccaaagg tatgtttcga atgatactaa   1740
cataacatag aacattttca ggaggaccct tgcttggagg gtaccgagct cagaaaaaat   1800
gactgctcca aagaagaagc gtaaggtacc ggtagaaaaa atgagtaaag gagaagaact   1860
tttcactgga gttgtcccaa ttcttgttga attagatggt gatgttaatg ggcacaaatt   1920
ttctgtcagt ggagagggtg aaggtgatgc aacatacgga aaacttaccc ttaaatttat   1980
ttgcactact ggaaaactac ctgttccatg ggtaagttta acatatata tactaactaa   2040
ccctgattat ttaaattttc agccaacact tgtcactact ttctgttatg gtgttcaatg   2100
cttctcgaga tacccagatc atatgaaacg gcatgacttt ttcaagagtg ccatgcccga   2160
aggttatgta caggaaagaa ctatatttt caaagatgac gggaactaca agacacgtaa   2220
gtttaaacag ttcggtacta actaaccata catatttaaa ttttcaggtg ctgaagtcaa   2280
gtttgaaggt gataccccttg ttaatagaat cgagttaaaa ggtattgatt ttaaagaaga   2340
tggaaacatt cttggacaca aattggaata caactataac tcacacaatg tatacatcat   2400
ggcagacaaa caaaagaatg gaatcaaagt tgtaagttta acatgatttt tactaactaa   2460
ctaatctgat ttaaattttc agaacttcaa aattagacac aacattgaag atggaagcgt   2520
tcaactagca gaccattatc aacaaaatac tccaattggc gatggccctg tcctttacc   2580
agacaaccat tacctgtcca cacaatctgc cctttcgaaa gatcccaacg aaaagagaga   2640
ccacatggtc cttcttgagt ttgtaacagc tgctgggatt acacatggca tggatgaact   2700
atacaaatag cattcgtaga attccaactg agcgccggtc gctaccatta ccaacttgtc   2760
tggtgtcaaa aataatagg gccgctgtca tcagagtaag tttaaactga gttctactaa   2820
ctaacgagta atatttaaat tttcagcatc tcgcgcccgt gcctctgact tctaagtcca   2880
```

-continued

| | |
|---|---|
| attactcttc aacatccta catgctcttt ctccctgtgc tcccaccccc tattttgtt | 2940 |
| attatcaaaa aaacttcttc ttaatttctt tgtttttag cttcttttaa gtcacctcta | 3000 |
| acaatgaaat tgtgtagatt caaaatagaa attaattcgt aataaaaagt cgaaaaaaat | 3060 |
| tgtgctccct cccccatta ataataattc tatcccaaaa tctacacaat gttctgtgta | 3120 |
| cacttcttat gtttttttta cttctgataa attttttttg aaacatcata gaaaaaaccg | 3180 |
| cacacaaaat accttatcat atgttacgtt tcagtttatg accgcaattt ttatttcttc | 3240 |
| gcacgtctgg gcctctcatg acgtcaaatc atgctcatcg tgaaaagtt ttggagtatt | 3300 |
| tttggaattt ttcaatcaag tgaaagttta tgaattaat tttcctgctt ttgctttttg | 3360 |
| ggggtttccc ctattgtttg tcaagagttt cgaggacggc gttttcttg ctaaaatcac | 3420 |
| aagtattgat gagcacgatg caagaaagat cggaagaagg tttgggttg aggctcagtg | 3480 |
| gaaggtgagt agaagttgat aatttgaaag tggagtagtg tctatggggt ttttgcctta | 3540 |
| aatgacagaa tacattccca atataccaaa cataactgtt tcctactagt cggccgtacg | 3600 |
| ggcccttcg tctcgcgcgt ttcggtgatg acggtgaaaa cctctgacac atgcagctcc | 3660 |
| cggagacggt cacagcttgt ctgtaagcgg atgccgggag cagacaagcc cgtcagggcg | 3720 |
| cgtcagcggg tgttggcggg tgtcggggct ggcttaacta tgcggcatca gagcagattg | 3780 |
| tactgagagt gcaccatatg cggtgtgaaa taccgcacag atgcgtaagg agaaaatacc | 3840 |
| gcatcaggcg gccttaaggg cctcgtgata cgcctatttt tataggttaa tgtcatgata | 3900 |
| ataatggttt cttagacgtc aggtggcact tttcgggga atgtgcgcgg aaccctatt | 3960 |
| tgttttatttt tctaaataca ttcaaatatg tatccgctca tgagacaata accctgataa | 4020 |
| atgcttcaat aatattgaaa aaggaagagt atgagtattc aacatttccg tgtcgccctt | 4080 |
| attccctttt ttgcggcatt ttgccttcct gttttgctc acccagaaac gctggtgaaa | 4140 |
| gtaaaagatg ctgaagatca gttgggtgca cgagtgggtt acatcgaact ggatctcaac | 4200 |
| agcggtaaga tccttgagag ttttcgcccc gaagaacgtt ttccaatgat gagcactttt | 4260 |
| aaagttctgc tatgtggcgc ggtattatcc cgtattgacg ccgggcaaga gcaactcggt | 4320 |
| cgccgcatac actattctca gaatgacttg gttgagtact caccagtcac agaaaagcat | 4380 |
| cttacggatg gcatgacagt aagagaatta tgcagtgctg ccataaccat gagtgataac | 4440 |
| actgcggcca acttacttct gacaacgatc ggaggaccga aggagctaac cgcttttttg | 4500 |
| cacaacatgg ggatcatgt aactcgcctt gatcgttggg aaccggagct gaatgaagcc | 4560 |
| ataccaaacg acgagcgtga caccacgatg cctgtagcaa tggcaacaac gttgcgcaaa | 4620 |
| ctattaactg gcgaactact tactctagct tcccggcaac aattaataga ctggatggag | 4680 |
| gcggataaag ttgcaggacc acttctgcgc tcggcccttc cggctggctg gtttattgct | 4740 |
| gataaatctg gagccggtga gcgtgggtct cgcggtatca ttgcagcact ggggccagat | 4800 |
| ggtaagccct cccgtatcgt agttatctac acgacgggga gtcaggcaac tatggatgaa | 4860 |
| cgaaatagac agatcgctga gataggtgcc tcactgatta gcattggta actgtcagac | 4920 |
| caagtttact catatatact ttagattgat ttaaaacttc attttaatt taaaaggatc | 4980 |
| taggtgaaga tcctttttga taatctcatg accaaaatcc cttaacgtga gttttcgttc | 5040 |
| cactgagcgt cagaccccgt agaaaagatc aaaggatctt cttgagatcc ttttttctg | 5100 |
| cgcgtaatct gctgcttgca acaaaaaaa ccaccgctac cagcggtggt ttgtttgccg | 5160 |
| gatcaagagc taccaactct ttttccgaag gtaactggct tcagcagagc gcagatacca | 5220 |
| aatactgtcc ttctagtgta gccgtagtta ggccaccact tcaagaactc tgtagcaccg | 5280 |

-continued

```
cctacatacc tcgctctgct aatcctgtta ccagtggctg ctgccagtgg cgataagtcg    5340
tgtcttaccg ggttggactc aagacgatag ttaccggata aggcgcagcg gtcgggctga    5400 acgggggtt cgtgcacaca gcccagcttg gagcgaacga cctacaccga actgagatac    5460
ctacagcgtg agcattgaga aagcgccacg cttcccgaag ggagaaaggc ggacaggtat    5520
ccggtaagcg gcaggtcgg aacaggagag cgcacgaggg agcttccagg gggaaacgcc    5580
tggtatcttt atagtcctgt cgggtttcgc cacctctgac ttgagcgtcg attttttgtga   5640 tgctcgtcag gggggcggag cctatggaaa acgccagca acgcggcctt tttacggttc    5700
ctggcctttt gctggccttt tgctcacatg ttctttcctg cgttatcccc tgattctgtg    5760
gataaccgta ttaccgcctt tgagtgagct gataccgctc gccgcagccg aacgaccgag    5820
cgcagcgagt cagtgagcga ggaagcggaa gagcgcccaa tacgcaaacc gcctctcccc    5880
gcgcgttggc cgattcatta atgcagctgg cacgacaggt ttcccgactg gaaagcgggc    5940
agtgagcgca acgcaattaa tgtgagttag ctcactcatt aggcacccca ggctttacac    6000
tttatgcttc cggctcgtat gttgtgtgga attgtgagcg gataacaatt tcacacagga    6060
aacagctatg accatgatta cgccaagctg taagtttaaa catgatctta ctaactaact    6120
attctcattt aaattttcag agcttaaaaa tggctgaaat cactcacaac gatggatacg    6180
ctaacaactt ggaaatgaaa ta                                            6202
```

<210> SEQ ID NO 9
<211> LENGTH: 5737
<212> TYPE: DNA
<213> ORGANISM: Artificial Sequence
<220> FEATURE:
<223> OTHER INFORMATION: plasmid pGF2009

<400> SEQUENCE: 9

```
accctctatt ccacttctct gttcatctgc tgcttctttt gtttaaccag ataaatctcc      60
ctcggggaaa accgtcaaaa aaaggcaaac taaatgcaaa cacgctctat agacaaaatg    120
tgtttggtct cgtcacgaat ggtgagagag aattggcctc cgccgcagag atcgcttgat    180
tattggcctc cagtgggcaa tgtcggggaa aaccaaacta ttgatgagag gtatcgacga    240
aaaatcaaca atgaccaact ttttgttaca gttttgttat aaatatgagt tttggatatt    300
ccattgcgta ttttttctttt ctactttcaa aaaatctgct ccaaccttta atggcttttc    360
ctgtcttgtc aaaatctgga tttttgaata tataatttt aaaaccatca aattcagcga    420
aatgaaatca tgtaatacaa ttttttattt tttccgactg ttgtgtattc catcaaacta    480
ttcaaaaaat caatataatg atttttttt cattttcgg actctagagg atccccgggg    540
attggccaaa ggacccaaag gtatgtttcg aatgatacta acataacata gaacattttc    600
aggaggaccc ttgcttggct agcaaaaatg cataaggttt tgctggcact gttctttatc    660
tttctggcac cagcatccgc actggcagtc tccgaaccgg cctgcaggat cgattttttg    720
caaattacga gcgttgtagg gggcggacga taggtcctat aggttttgta tatcatcatt    780
cattcattca ttggtacatt catttaccca ccttcctctt tctgagcttc tctggagttc    840
tgtgcttcct ttttcccctta tctttatact gtaatttta actttcaggc attgattgga    900
tccccgggat tggccaaagg acccaaaggt atgtttcgaa tgatactaac ataacataga    960
acattttcag gaggaccctt gcttggaggg taccgagctc agaaaaaatg actgctccaa    1020
agaagaagcg taaggtaccg gtagaaaaaa tgagtaaagg agaagaactt ttcactggag    1080
```

```
ttgtcccaat tcttgttgaa ttagatggtg atgttaatgg gcacaaattt tctgtcagtg    1140
gagagggtga aggtgatgca acatacggaa aacttaccct taaatttatt tgcactactg    1200
gaaaactacc tgttccatgg gtaagtttaa acatatatat actaactaac cctgattatt    1260
taaattttca gccaacactt gtcactactt tctgttatgg tgttcaatgc ttctcgagat    1320
acccagatca tatgaaacgg catgactttt tcaagagtgc catgcccgaa ggttatgtac    1380
aggaaagaac tatattttc aaagatgacg ggaactacaa gacacgtaag tttaaacagt     1440
tcggtactaa ctaaccatac atatttaaat tttcaggtgc tgaagtcaag tttgaaggtg    1500 ataccttgt taatagaatc gagttaaaag gtattgattt taaagaagat ggaaacattc     1560
ttggacacaa attggaatac aactataact cacacaatgt atacatcatg gcagacaaac    1620
aaaagaatgg aatcaaagtt gtaagtttaa acatgatttt actaactaac taatctgatt    1680
taaattttca gaacttcaaa attagacaca acattgaaga tggaagcgtt caactagcag    1740
accattatca acaaaatact ccaattggcg atggccctgt ccttttacca gacaaccatt    1800
acctgtccac acaatctgcc ctttcgaaag atcccaacga aaagagagac cacatggtcc    1860
ttcttgagtt tgtaacagct gctgggatta cacatggcat ggatgaacta tacaaatagc    1920
attcgtagaa ttccaactga gcgccggtcg ctaccattac caacttgtct ggtgtcaaaa    1980
ataatagggg ccgctgtcat cagagtaagt ttaaactgag ttctactaac taacgagtaa    2040
tatttaaatt ttcagcatct cgcgcccgtg cctctgactt ctaagtccaa ttactcttca    2100
acatccctac atgctctttc tccctgtgct cccacccct atttttgtta ttatcaaaaa     2160
aacttcttct taatttcttt gttttttagc ttcttttaag tcacctctaa caatgaaatt    2220
gtgtagattc aaaaatagaa ttaattcgta ataaaaagtc gaaaaaaatt gtgctccctc    2280
cccccattaa taataattct atcccaaaat ctacacaatg ttctgtgtac acttcttatg    2340 tttttttac ttctgataaa tttttttga aacatcatag aaaaaaccgc acacaaaata      2400
ccttatcata tgttacgttt cagtttatga ccgcaatttt tatttcttcg cacgtctggg    2460
cctctcatga cgtcaaatca tgctcatcgt gaaaagtttt tggagtattt ttggaatttt    2520
tcaatcaagt gaaagtttat gaaattaatt ttcctgcttt tgcttttttgg gggtttcccc   2580 tattgtttgt caagagtttc gaggacggcg ttttcttgc taaaatcaca agtattgatg     2640
agcacgatgc aagaaagatc ggaagaaggt tgggtttga ggctcagtgg aaggtgagta     2700
gaagttgata atttgaaagt ggagtagtgt ctatggggtt tttgccttaa atgacagaat    2760
acattcccaa tataccaaac ataactgttt cctactagtc ggccgtacgg gcccttcgt     2820 ctcgcgcgtt tcggtgatga cggtgaaaac ctctgacaca tgcagctccc ggagacggtc    2880
acagcttgtc tgtaagcgga tgccgggagc agacaagccc gtcagggcgc gtcagcgggt    2940
gttggcgggt gtcggggctg gcttaactat gcggcatcag agcagattgt actgagagtg    3000
caccatatgc ggtgtgaaat accgcacaga tgcgtaagga gaaaataccg catcaggcgg    3060
ccttaagggc ctcgtgatac gcctattttt ataggttaat gtcatgataa taatggtttc    3120
ttagacgtca ggtggcactt tcggggaaa tgtgcgcgga accctatttt gtttattttt     3180
ctaaatacat tcaaatatgt atccgctcat gagacaataa ccctgataaa tgcttcaata    3240
atattgaaaa aggaagagta tgagtattca acatttccgt gtcgccctta ttccctttt     3300 tgcggcattt tgccttcctg tttttgctca cccagaaacg ctggtgaaag taaaagatgc    3360
tgaagatcag ttgggtgcac gagtgggtta catcgaactg gatctcaaca gcggtaagat    3420
ccttgagagt tttcgccccg aagaacgttt tccaatgatg agcacttta aagttctgct     3480
```

```
atgtggcgcg gtattatccc gtattgacgc cgggcaagag caactcggtc gccgcataca    3540
ctattctcag aatgacttgg ttgagtactc accagtcaca gaaaagcatc ttacggatgg    3600
catgacagta agagaattat gcagtgctgc cataaccatg agtgataaca ctgcggccaa    3660
cttacttctg acaacgatcg gaggaccgaa ggagctaacc gcttttttgc acaacatggg    3720
ggatcatgta actcgccttg atcgttggga accggagctg aatgaagcca taccaaacga    3780
cgagcgtgac accacgatgc ctgtagcaat ggcaacaacg ttgcgcaaac tattaactgg    3840
cgaactactt actctagctt cccggcaaca attaatagac tggatggagg cggataaagt    3900
tgcaggacca cttctgcgct cggcccttcc ggctggctgg tttattgctg ataaatctgg    3960
agccggtgag cgtgggtctc gcggtatcat tgcagcactg gggccagatg gtaagccctc    4020
ccgtatcgta gttatctaca cgacggggag tcaggcaact atggatgaac gaaatagaca    4080
gatcgctgag ataggtgcct cactgattaa gcattggtaa ctgtcagacc aagtttactc    4140
atatatactt tagattgatt taaaacttca tttttaattt aaaaggatct aggtgaagat    4200
cctttttgat aatctcatga ccaaaatccc ttaacgtgag ttttcgttcc actgagcgtc    4260
agacccgta gaaaagatca aaggatcttc ttgagatcct ttttttctgc gcgtaatctg    4320
ctgcttgcaa acaaaaaaac caccgctacc agcggtggtt tgtttgccgg atcaagagct    4380
accaactctt tttccgaagg taactggctt cagcagagcg cagataccaa atactgtcct    4440
tctagtgtag ccgtagttag gccaccactt caagaactct gtagcaccgc ctacatacct    4500
cgctctgcta atcctgttac cagtggctgc tgccagtggc gataagtcgt gtcttaccgg    4560
gttggactca agacgatagt taccggataa ggcgcagcgg tcgggctgaa cggggggttc    4620
gtgcacacag cccagcttgg agcgaacgac ctacaccgaa ctgagatacc tacagcgtga    4680
gcattgagaa agcgccacgc ttcccgaagg gagaaaggcg gacaggtatc cggtaagcgg    4740
cagggtcgga acaggagagc gcacgaggga gcttccaggg ggaaacgcct ggtatcttta    4800
tagtcctgtc gggtttcgcc acctctgact tgagcgtcga ttttgtgat gctcgtcagg    4860
ggggcggagc ctatggaaaa acgccagcaa cgcggccttt ttacggttcc tggccttttg    4920
ctggcctttt gctcacatgt tctttcctgc gttatcccct gattctgtgg ataaccgtat    4980
taccgccttt gagtgagctg ataccgctcg ccgcagccga acgaccgagc gcagcgagtc    5040
agtgagcgag gaagcggaag agcgcccaat acgcaaaccg cctctccccg cgcgttggcc    5100
gattcattaa tgcagctggc acgacaggtt tcccgactgg aaagcgggca gtgagcgcaa    5160
cgcaattaat gtgagttagc tcactcatta ggcaccccag gctttacact ttatgcttcc    5220
ggctcgtatg ttgtgtggaa ttgtgagcgg ataacaattt cacacaggaa acagctatga    5280
ccatgattac gccaagctgt aagtttaaac atgatcttac taactaacta ttctcattta    5340
aattttcaga gcttaaaaat ggctgaaatc actcacaacg atggatacgc taacaacttg    5400
gaaatgaaat aagcttcatg cgtcttcttg attactgtag atgtttggca acttattttt    5460
acataaaaac gttttcattc attatttcca tcattcattt atctttctgt gttttagtt    5520
agttttagct agttttttc taaattccta actttaaaaa atctggaaaa gaaaattaaa    5580
aaattttgtc cctattattt attttattac tggaaaatct tcaaacagga aacccaccg    5640
cgttttgctt attgctgtat ttatgaaaaa aaaacaatc aatattggtc aagtaaataa    5700
gaaaaaatta acgaatctct atctgacacc agatgcg                           5737
```

<210> SEQ ID NO 10

<210> LENGTH: 6157
<212> TYPE: DNA
<213> ORGANISM: Artificial Sequence
<220> FEATURE:
<223> OTHER INFORMATION: plasmid pGF2013

<400> SEQUENCE: 10

```
ctcacccaga aacgctggtg aaagtaaaag atgctgaaga tcagttgggt gcacgagtgg      60
gttacatcga actggatctc aacagcggta agatccttga gagttttcgc cccgaagaac     120
gttttccaat gatgagcact tttaaagttc tgctatgtgg cgcggtatta tcccgtattg     180
acgccgggca agagcaactc ggtcgccgca tacactattc tcagaatgac ttggttgagt     240
actcaccagt cacagaaaag catcttacgg atggcatgac agtaagagaa ttatgcagtg     300
ctgccataac catgagtgat aacactgcgg ccaacttact tctgacaacg atcggaggac     360
cgaaggagct aaccgctttt ttgcacaaca tgggggatca tgtaactcgc cttgatcgtt     420
gggaaccgga gctgaatgaa gccataccaa acgacgagcg tgacaccacg atgcctgtag     480
caatggcaac aacgttgcgc aaactattaa ctggcgaact acttactcta gcttcccggc     540
aacaattaat agactggatg gaggcggata agttgcagg accacttctg cgctcggccc     600
ttccggctgg ctggtttatt gctgataaat ctggagccgg tgagcgtggg tctcgcggta     660
tcattgcagc actggggcca gatggtaagc cctcccgtat cgtagttatc tacacgacgg     720
ggagtcaggc aactatggat gaacgaaata gacagatcgc tgagataggt gcctcactga     780
ttaagcattg gtaactgtca gaccaagttt actcatatat actttagatt gatttaaaac     840
ttcattttta atttaaaagg atctaggtga agatcctttt tgataatctc atgaccaaaa     900
tcccttaacg tgagttttcg ttccactgag cgtcagaccc cgtagaaaag atcaaaggat     960
cttcttgaga tccttttttt ctgcgcgtaa tctgctgctt gcaaacaaaa aaaccaccgc    1020
taccagcggt ggtttgtttg ccggatcaag agctaccaac tcttttccg aaggtaactg    1080
gcttcagcag agcgcagata ccaaatactg tccttctagt gtagccgtag ttaggccacc    1140
acttcaagaa ctctgtagca ccgcctacat acctcgctct gctaatcctg ttaccagtgg    1200
ctgctgccag tggcgataag tcgtgtctta ccgggttgga ctcaagacga tagttaccgg    1260
ataaggcgca gcggtcgggc tgaacggggg gttcgtgcac acagcccagc ttggagcgaa    1320
cgacctacac cgaactgaga tacctacagc gtgagcattg agaaagcgcc acgcttcccg    1380
aagggagaaa ggcggacagg tatccggtaa gcggcagggt cggaacagga gagcgcacga    1440
gggagcttcc agggggaaac gcctggtatc tttatagtcc tgtcgggttt cgccacctct    1500
gacttgagcg tcgatttttg tgatgctcgt caggggggcg gagcctatgg aaaaacgcca    1560
gcaacgcggc cttttacgg ttcctggcct tttgctggcc ttttgctcac atgttctttc    1620
ctgcgttatc ccctgattct gtggataacc gtattaccgc ctttgagtga gctgataccg    1680
ctcgccgcag ccgaacgacc gagcgcagcg agtcagtgag cgaggaagcg gaagagcgcc    1740
caatacgcaa accgcctctc cccgcgcgtt ggccgattca ttaatgcagc tggcacgaca    1800
ggtttcccga ctggaaagcg ggcagtgagc gcaacgcaat taatgtgagt tagctcactc    1860
attaggcacc ccaggcttta cactttatgc ttccggctcg tatgttgtgt ggaattgtga    1920
gcggataaca atttcacaca ggaaacagct atgaccatga ttacgccaag ctgtaagttt    1980
aaacatgatc ttactaacta actattctca tttaaatttt cagagcttaa aaatggctga    2040
aatcactcac aacgatggat acgctaacaa cttggaaatg aaataagctt gcatgcaagg    2100
ttagttgcct gtttaagcat tatccccgca tgtagcttgt tcggcaccgt taaaaatgct    2160
```

```
gagtaatcag cttttagaa tttaaaatat taaactttta aaattgcaac aaacatcgac    2220
aaatattcaa gaggcgaatg atatcgggaa tttcgattga acgaaactg ttttgaaatt    2280
caaaaagtat tttcaaagta ttgtccgcaa ggcacatcac gcaaacttgc agaatctacc   2340
gtatcccata cattttata gttttcccct cagtttttaa aattaaaaac gctgaaaaag    2400
cgattaaatt tatttaaatg catcgttcga ataaaataaa gtttatcttt tgataaaaac   2460
atgagttcc tttggagaaa agtagggatt tcgccttca aaaattatt tcgtgcagga     2520
tgctattttc gtggcgaaac ccatactcaa gagctcatgc gtcttcttga ttactgtaga  2580
tgtttggcaa cttattttta cataaaaacg ttttcattca ttatttccat cattcattta  2640
tctttctgtg tttttagtta gttttagcta gttttttct aaattcctaa ctttaaaaaa   2700
tctggaaaag aaaattaaaa aattttgtcc ctattattta ttttattact ggaaaatctt  2760
caaacaggaa aacccaccgc gttttgctta ttgctgtatt tatgaaaaaa aaacaatca   2820
atattggtca agtaaataag aaaaaattaa cgaatctcta tctgacacca gatgcgaccc  2880
tctattccac ttctctgttc atctgctgct tcttttgttt aaccagataa atctccctcg  2940
gggaaaaccg tcaaaaaaag gcaaactaaa tgcaaacacg ctctatagac aaaatgtgtt  3000
tggtctcgtc acgaatggtg agagagaatt ggcctccgcc gcagagatcg cttgattatt  3060
ggcctccagt gggcaatgtc ggggaaaacc aaactattga tgagaggtat cgacgaaaaa  3120
tcaacaatga ccaactttt gttacagttt tgttataaat atgagttttg gatattccat   3180
tgcgtatttt tcttttctac tttcaaaaaa tctgctccaa cctttaatgg cttttcctgt  3240
cttgtcaaaa tctggatttt tgaatatata attttaaaa ccatcaaatt cagcgaaatg   3300
aaatcatgta atacaatttt ttattttttc cgactgttgt gtattccatc aaactattca  3360
aaaaatcaat ataatgattt ttttttcatt tttcggactc tagaggatcc ccggggattg  3420
gccaaaggac ccaaaggtat gtttcgaatg atactaacat aacatagaac attttcagga  3480
ggacccttgc ttggctagca aaatgcata aggttttgct ggcactgttc tttatctttc   3540
tggcaccagc atccgcactg gcagtctccg aaccggcctg caggatcgat ttttgcaaa   3600
ttacgagcgt tgtaggggc ggacgatagg tcctataggt tttgtatatc atcattcat    3660
cattcattgg tacattcatt tacccacctt cctctttctg agcttctctg gagttctgtg  3720
cttcctttt ccccttatctt tatactgtaa tttttaactt tcaggcattg attggatccc   3780
cgggattggc caaggaccc aaaggtatgt ttcgaatgat actaacataa catagaacat    3840
tttcaggagg acccttgctt ggagggtacc ggtagaaaaa atgagtaaag gagaagaact   3900
tttcactgga gttgtcccaa ttcttgttga attagatggt gatgttaatg ggcacaaatt   3960
ttctgtcagt ggagagggtg aaggtgatgc aacatacgga aaacttaccc ttaaatttat   4020
ttgcactact ggaaaactac ctgttccatg gtaagttta acatatata tactaactaa     4080
ccctgattat ttaaatttc agccaacact tgtcactact ttctgttatg gtgttcaatg   4140
cttctcgaga tacccagatc atatgaaacg gcatgacttt tcaagagtg ccatgcccga    4200
aggttatgta caggaaagaa ctatattttt caaagatgac gggaactaca agacacgtaa   4260
gtttaaacag ttcggtacta actaaccata catatttaaa ttttcaggtg ctgaagtcaa   4320
gtttgaaggt gataccttg ttaatagaat cgagttaaaa ggtattgatt ttaaagaaga    4380
tggaaacatt cttggacaca aattggaata caactataac tcacacaatg tatacatcat   4440
ggcagacaaa caaaagaatg gaatcaaagt tgtaagttta aacatgattt tactaactaa   4500
```

```
ctaatctgat ttaaattttc agaacttcaa aattagacac aacattgaag atggaagcgt    4560
tcaactagca gaccattatc aacaaaatac tccaattggc gatggccctg tccttttacc    4620
agacaaccat tacctgtcca cacaatctgc cctttcgaaa gatcccaacg aaaagagaga    4680
ccacatggtc cttcttgagt ttgtaacagc tgctgggatt acacatggca tggatgaact    4740
atacaaatag cattcgtaga attccaactg agcgccggtc gctaccatta ccaacttgtc    4800
tggtgtcaaa ataataggg gccgctgtca tcagagtaag tttaaactga gttctactaa    4860
ctaacgagta atatttaaat tttcagcatc tcgcgcccgt gcctctgact tctaagtcca    4920
attactcttc aacatcccta catgctcttt ctccctgtgc tcccacccc tattttgtt     4980 attatcaaaa aaacttcttc ttaatttctt tgttttttag cttcttttaa gtcacctcta    5040
acaatgaaat tgtgtagatt caaaaataga attaattcgt aataaaaagt cgaaaaaaat    5100
tgtgctccct cccccatta ataataattc tatcccaaaa tctacacaat gttctgtgta     5160
cacttcttat gttttttta cttctgataa attttttttg aaacatcata gaaaaaccg     5220 cacacaaaat accttatcat atgttacgtt tcagtttatg accgcaattt ttatttcttc    5280
gcacgtctgg gcctctcatg acgtcaaatc atgctcatcg tgaaaagtt ttggagtatt     5340 tttgaatttt tcaatcaag tgaaagttta tgaaattaat tttcctgctt ttgcttttg      5400 ggggtttccc ctattgttg tcaagagttt cgaggacggc gttttcttg ctaaaatcac       5460 aagtattgat gagcacgatg caagaaagat cggaagaagg tttgggtttg aggctcagtg    5520
gaaggtgagt agaagttgat aatttgaaag tggagtagtg tctatggggt ttttgcctta    5580
aatgacagaa tacattccca atataccaaa cataactgtt tcctactagt cggccgtacg    5640
ggccctttcg tctcgcgcgt ttcggtgatg acggtgaaaa cctctgacac atgcagctcc    5700
cggagacggt cacagcttgt ctgtaagcgg atgccgggag cagacaagcc cgtcagggcg    5760
cgtcagcggg tgttggcggg tgtcggggct ggcttaacta tgcggcatca gagcagattg    5820
tactgagagt gcaccatatg cggtgtgaaa taccgcacag atgcgtaagg agaaaatacc    5880
gcatcaggcg gccttaaggg cctcgtgata cgcctatttt tataggttaa tgtcatgata    5940
ataatggttt cttagacgtc aggtggcact tttcggggaa atgtgcgcgg aaccccctatt   6000 tgtttatttt tctaaataca ttcaaatatg tatccgctca tgagacaata accctgataa    6060
atgcttcaat aatattgaaa aaggaagagt atgagtattc aacatttccg tgtcgccctt    6120 attcccttt ttgcggcatt ttgccttcct gttttttg                             6157
```

<210> SEQ ID NO 11
<211> LENGTH: 5692
<212> TYPE: DNA
<213> ORGANISM: Artificial Sequence
<220> FEATURE:
<223> OTHER INFORMATION: plasmid pGF2014

<400> SEQUENCE: 11

```
taaacatata tatactaact aaccctgatt atttaaattt tcagccaaca cttgtcacta      60
ctttctgtta tggtgttcaa tgcttctcga gatacccaga tcatatgaaa cggcatgact     120
ttttcaagag tgccatgccc gaaggttatg tacaggaaag aactatattt ttcaaagatg     180
acgggaacta caagacacgt aagtttaaac agttcggtac taactaacca tacatattta     240
aattttcagg tgctgaagtc aagtttgaag gtgataccct tgttaataga atcgagttaa     300
aaggtattga ttttaaagaa gatggaaaca ttcttggaca caaattggaa tacaactata    360
actcacacaa tgtatacatc atggcagaca acaaaagaa tggaatcaaa gttgtaagtt     420
```

-continued

```
taaacatgat tttactaact aactaatctg atttaaattt tcagaacttc aaaattagac      480
acaacattga agatggaagc gttcaactag cagaccatta tcaacaaaat actccaattg      540
gcgatggccc tgtcctttta ccagacaacc attacctgtc cacacaatct gcccttttcga    600 aagatcccaa cgaaaagaga gaccacatgg tccttcttga gtttgtaaca gctgctggga     660
ttacacatgg catggatgaa ctatacaaat agcattcgta gaattccaac tgagcgccgg     720
tcgctaccat taccaacttg tctggtgtca aaataatag gggccgctgt catcagagta      780
agtttaaact gagttctact aactaacgag taatatttaa attttcagca tctcgcgccc     840
gtgcctctga cttctaagtc caattactct tcaacatccc tacatgctct ttctccctgt     900
gctcccaccc cctattttg ttattatcaa aaaacttct tcttaatttc tttgtttttt       960
agcttctttt aagtcacctc taacaatgaa attgtgtaga ttcaaaaata gaattaattc     1020
gtaataaaaa gtcgaaaaaa attgtgctcc ctcccccat taataataat tctatcccaa      1080
aatctacaca atgttctgtg tacacttctt atgttttttt tacttctgat aaattttttt     1140
tgaaacatca tagaaaaaac cgcacacaaa ataccttatc atatgttacg tttcagttta    1200
tgaccgcaat tttattttct tcgcacgtct gggcctctca tgacgtcaaa tcatgctcat    1260
cgtgaaaaag ttttggagta tttttggaat ttttcaatca agtgaaagtt tatgaaatta    1320 atttcctgc ttttgctttt tggggttc ccctattgtt tgtcaagagt ttcgaggacg        1380 gcgttttct tgctaaaatc acaagtattg atgagcacga tgcaagaaag atcggaagaa      1440
ggtttgggtt tgaggctcag tggaaggtga gtagaagttg ataatttgaa agtggagtag    1500
tgtctatggg gttttttgcct taaatgacag aatacattcc caatataccca aacataactg  1560 tttcctacta gtcggccgta cgggcccttt cgtctcgcgc gtttcggtga tgacggtgaa    1620
aacctctgac acatgcagct cccggagacg gtcacagctt gtctgtaagc ggatgccggg    1680
agcagacaag cccgtcaggg cgcgtcagcg ggtgttggcg ggtgtcgggg ctggcttaac    1740
tatgcggcat cagagcagat tgtactgaga gtgcaccata tgcggtgtga ataccgcac     1800 agatgcgtaa ggagaaaata ccgcatcagg cggccttaag ggcctcgtga tacgcctatt    1860
tttataggtt aatgtcatga taataatggt ttccttagacg tcaggtggca cttttcgggg   1920
aaatgtgcgc ggaaccccta tttgtttatt tttctaaata cattcaaata tgtatccgct    1980
catgagacaa taaccctgat aaatgcttca ataatattga aaaggaaga gtatgagtat     2040 tcaacatttc cgtgtcgccc ttattccctt ttttgcggca ttttgccttc ctgttttgtgc   2100 tcacccagaa acgctggtga agtaaaaaga tgctgaagat cagttgggtg cacgagtggg    2160
ttacatcgaa ctggatctca acagcggtaa gatccttgag agttttcgcc ccgaagaacg    2220
ttttccaatg atgagcactt ttaaagttct gctatgtggc gcggtattat cccgtattga    2280
cgccgggcaa gagcaactcg gtcgccgcat acactattct cagaatgact tggttgagta    2340
ctcaccagtc acagaaaagc atcttacgga tggcatgaca gtaagagaat tatgcagtgc    2400
tgccataacc atgagtgata acactgcggc caacttactt ctgacaacga tcggaggacc    2460
gaaggagcta accgcttttt tgcacaacat ggggatcat gtaactcgcc ttgatcgttg    2520
ggaaccggag ctgaatgaag ccataccaaa cgacgagcgt gacaccacga tgcctgtagc    2580
aatggcaaca acgttgcgca aactattaac tggcgaacta cttactctag cttcccggca   2640
acaattaata gactgatgg aggcggataa agttgcagga ccacttctgc gctcggccct    2700
tccggctggc tggtttattg ctgataaatc tggagccggt gagcgtgggt ctcgcggtat   2760
```

-continued

```
cattgcagca ctggggccag atggtaagcc ctcccgtatc gtagttatct acacgacggg    2820
gagtcaggca actatggatg aacgaaatag acagatcgct gagataggtg cctcactgat    2880
taagcattgg taactgtcag accaagttta ctcatatata ctttagattg atttaaaact    2940
tcatttttaa tttaaaagga tctaggtgaa gatccttttt gataatctca tgaccaaaat    3000
cccttaacgt gagttttcgt tccactgagc gtcagacccc gtagaaaaga tcaaaggatc    3060
ttcttgagat ccttttttc tgcgcgtaat ctgctgcttg caaacaaaaa aaccaccgct    3120
accagcggtg gtttgtttgc cggatcaaga gctaccaact cttttttccga aggtaactgg    3180 cttcagcaga gcgcagatac caaatactgt ccttctagtg tagccgtagt taggccacca    3240
cttcaagaac tctgtagcac cgcctacata cctcgctctg ctaatcctgt taccagtggc    3300
tgctgccagt ggcgataagt cgtgtcttac cgggttggac tcaagacgat agttaccgga    3360
taaggcgcag cggtcgggct gaacggggggg ttcgtgcaca cagcccagct tggagcgaac    3420
gacctacacc gaactgagat acctacagcg tgagcattga gaaagcgcca cgcttcccga    3480
agggagaaag gcggacaggt atccggtaag cggcagggtc ggaacaggag agcgcacgag    3540
ggagcttcca gggggaaacg cctggtatct ttatagtcct gtcgggtttc gccacctctg    3600
acttgagcgt cgatttttgt gatgctcgtc agggggggcgg agcctatgga aaaacgccag    3660
caacgcggcc ttttttacggt tcctggcctt ttgctggcct tttgctcaca tgttctttcc    3720
tgcgttatcc cctgattctg tggataaccg tattaccgcc tttgagtgag ctgataccgc    3780
tcgccgcagc cgaacgaccg agcgcagcga gtcagtgagc gaggaagcgg aagagcgccc    3840
aatacgcaaa ccgcctctcc ccgcgcgttg gccgattcat taatgcagct ggcacgacag    3900
gtttcccgac tggaaagcgg gcagtgagcg caacgcaatt aatgtgagtt agctcactca    3960
ttaggcaccc caggctttac actttatgct tccggctcgt atgttgtgtg gaattgtgag    4020
cggataacaa tttcacacag gaaacagcta tgaccatgat tacgccaagc tgtaagttta    4080
aacatgatct tactaactaa ctattctcat ttaaattttc agagcttaaa aatggctgaa    4140
atcactcaca acgatggata cgctaacaac ttggaaatga ataagcttc atgcgtcttc    4200 ttgattactg tagatgtttg gcaacttatt tttacataaa aacgttttca ttcattattt    4260
ccatcattca tttatctttc tgtgttttta gttagttta gctagttttt ttctaaattc    4320
ctaactttaa aaaatctgga aagaaaatt aaaaaatttt gtccctatta tttattttat    4380
tactggaaaa tcttcaaaca ggaaaaccca ccgcgttttg cttattgctg tatttatgaa    4440
aaaaaaaaca atcaatattg gtcaagtaaa taagaaaaaa ttaacgaatc tctatctgac    4500
accagatgcg accctctatt ccacttctct gttcatctgc tgcttctttt gtttaaccag    4560
ataaatctcc ctcggggaaa accgtcaaaa aaggcaaac taaatgcaaa cacgctctat    4620
agacaaaatg tgtttggtct cgtcacgaat ggtgagagag aattggcctc cgccgcagag    4680
atcgcttgat tattggcctc cagtgggcaa tgtcgggaa accaaacta ttgatgagag    4740 gtatcgacga aaaatcaaca atgaccaact ttttgttaca gttttgttat aaatatgagt    4800
tttggatatt ccattgcgta ttttttcttt ctactttcaa aaaatctgct ccaaccttta    4860
atggcttttc ctgtcttgtc aaaatctgga ttttgaata tataattttt aaaaccatca    4920
aattcagcga aatgaaatca tgtaatacaa ttttttattt tttccgactg ttgtgtattc    4980
catcaaacta ttcaaaaaat caatataatg attttttttt catttttcgg actctagagg    5040
atccccgggg attggccaaa ggacccaaag gtatgtttcg aatgatacta acataacata    5100
gaacattttc aggaggaccc ttgcttggct agcaaaaatg cataaggttt tgctggcact    5160
```

-continued

```
gttctttatc tttctggcac cagcatccgc actggcagtc tccgaaccgg cctgcaggat    5220 cgatttttg  caaattacga gcgttgtagg gggcggacga taggtcctat aggttttgta    5280
tatcatcatt cattcattca ttggtacatt catttaccca ccttcctctt tctgagcttc    5340
tctggagttc tgtgcttcct ttttccctta tctttatact gtaattttta actttcaggc    5400
attgattgga tccccgggat tggccaaagg acccaaaggt atgtttcgaa tgatactaac    5460
ataacataga acattttcag gaggaccctt gcttggaggg taccggtaga aaaaatgagt    5520
aaaggagaag aacttttcac tggagttgtc ccaattcttg ttgaattaga tggtgatgtt    5580
aatgggcaca aattttctgt cagtggagag ggtgaaggtg atgcaacata cggaaaactt    5640
acccttaaat ttatttgcac tactggaaaa ctacctgttc catgggtaag tt           5692
```

EXPRESSION OF DNA OR PROTEINS IN C. ELEGANS

RELATED APPLICATIONS

This application claims priority under 35 U.S.C. §119(a) from U.K. Patent Application Serial No. 9906018.8, filed on Mar. 16, 2000, entitled EXPRESSION OF DNA OR PROTEINS IN C. ELEGANS. The entire contents of the above-identified application are hereby expressly incorporated by reference.

FIELD OF THE INVENTION

The present invention relates to the expression of DNA, genes, cDNAs, proteins, peptides and parts thereof in the excretory canal of the nematode worm C. elegans. In particular, the invention relates to promoter sequences which are capable of directing tissue-specific gene expression in the excretory canal of C. elegans, to expression vectors containing the promoter sequences, to transgenic C. elegans specifically expressing reporter genes in the excretory canal, to methods of identifying chemical agents that affect the morphology of the excretory canal and to use of these agents in the pharmacological treatment of diseases for which the C. elegans excretory canal serves as a model.

BACKGROUND OF THE INVENTION

The C. elegans Excretory Cell

The excretory system of the nematode C. elegans consists of three cells: a single large excretory cell, a duct cell and a pore cell that interfaces with the duct to the main body hypodermis. The excretory cell is the largest mononucleate cell in C. elegans. The nucleus and cell body of the excretory cell is situated at the terminal bulb of the pharynx. The cell itself is shaped in an H-form, with the two arms situated along the lateral lines for almost the entire length of the worm, and slightly dorsal. The excretory cell is polarized, having an apical domain facing the lumen of the excretory canal and a basal domain facing outside. The structure and the organization of the C. elegans excretory system suggest that it may be used for osmoregulation and can therefore be considered as a model for the vertebrate nephron.

Various mutant C. elegans have been reported which have an aberrant phenotype in the excretory canal. These aberrant phenotypes include cyst formation, short canals and branched canals. Various mutations affecting the excretory canal can be traced back in C. elegans II, ed. Riddle, Blumenthal, Meyer and Priess, Cold Spring Harbor Laboratory Press, 1997.

Drug Discovery in Growth Cone Steering.

Regulation of cell motility, cell shape and the outgrowth of axons or other cell outgrowths are all essential processes in the morphogenesis and function of both unicellular and multicellular organisms. Furthermore, the control of these processes is disturbed in a variety of diseases in which receptors, extra-cellular signals and intra-cellular pathways are over- or under-stimulated. The discovery of new genes, proteins and peptides that are involved in these processes and chemical entities which modulate them would very much help the understanding of these processes. Accordingly, there is a need to develop new methods for the discovery of novel molecules involved in the cell motility, cell shape and cell outgrowth process, and to establish their function. In addition, since malfunction of these biological processes can lead to disease there is also a need to discover chemical entities which modulate these processes which may be useful as pharmaceuticals. Diseases associated with cell motility, cell shape and cell outgrowth include cancerous disease, more particularly tumor formation, tumor metastasis and vascularisation of tumors.

Drug Discovery in Renal Diseases.

In the drug discovery process it is established practice to develop a model of a disease which can be used in the development of assays to screen for compounds with potential pharmaceutical activity. For kidney diseases, and more specifically kidney cyst formation, two different types of disease models currently exist; models based on cell cultures of renal epithelial cells and mouse models. Although these systems have been presented as models for cystic diseases, such as autosomal dominant polycystic kidney disease (ADPKD), they have several disadvantages.

The models based on cell cultures can never be compared with a live multicellular organism. Where aberrant growth indicative of cyst formation has been observed in cultures of different cells, it has proven difficult to develop efficient compound screens from these models. Furthermore, even if chemicals can be discovered that modulate cell growth and hence cyst formation in culture, it remains difficult to prove that these compounds will have analogous effects in the renal systems of multicellular organisms.

The developed mouse models for renal cyst diseases have the disadvantage that they are not suitable for middle to high throughput screening for the discovery of pharmacological compounds. Accordingly, there remains a clear need for an alternative model of renal diseases which more accurately models the renal systems of multicellular organisms but which is practical for use in middle to high throughput screening.

SUMMARY OF THE INVENTION

The present invention relates to the use of the C. elegans excretory cell in the drug discovery process. The C. elegans excretory canal is an efficient tool to study various developmental biological features; it is formed during the larval stages of the nematode and the canals are observed to grow along the animal in early development. Hence, the development of the excretory canal is an efficient tool to study growth cone steering and defects that might arise during its development and the excretory canal can be used as a model for the development of drug screens in the area of growth cone steering and directional outgrowth.

The C. elegans excretory cell and excretory canal can also be considered as a model of the human kidney nephron. The excretory canal has analogous apical-basal polarities as can be found in certain kidney cells and which are relevant for cellular function. Hence, studying the excretory canal may help to develop new tools against kidney diseases. Furthermore, the excretory canal can be used as a model for the development of drug screens in the area of kidney diseases.

In order to exploit the potential of the C. elegans excretory cell and excretory canal both as a disease model and in the development of drug screens it would be advantageous to be able to express any gene or cDNA of interest, including reporter genes, specifically in the excretory cell and excretory canal. To achieve this would require the identification of a tissue-specific promoter which is active in the excretory cell.

The present inventors have identified, through the use of biochemical, molecular biology and transgenic techniques, a promoter fragment that specifically directs transcription in the C. elegans excretory cell in a very efficient way. From this promoter fragment several deletions have been generated that still promote transcription, and hence gene expression, in the excretory cell of C. elegans. These promoter fragments are useful tools as they can be used to direct specific expression of any DNA fragment of interest in the excretory cell and excretory canal.

Accordingly, in a first aspect the invention provides a DNA fragment which is capable of functioning as a promoter directing gene expression in the excretory cell of C. elegans, which DNA fragment comprises the sequence of nucleotides set forth in any one of SEQ ID NO:2, SEQ ID NO:3, SEQ ID NO:4, SEQ ID NO:5, SEQ ID NO:6, SEQ ID NO:7, or a fragment thereof in the absence of any other sequence of consecutive nucleotides from the C. elegans genome (i.e., an isolated DNA fragment).

According to another aspect of the invention, an isolated nucleic acid molecule, is provided. The isolated nucleic acid molecule can comprise: (a) nucleic acid molecules which hybridize under stringent conditions to a molecule consisting of a nucleic acid having a sequence selected from the group consisting of SEQ ID NO:2, SEQ ID NO:3, SEQ ID NO:4, SEQ ID NO:5, SEQ ID NO:6, and SEQ ID NO:7, and which direct expression of a heterologous DNA fragment to the excretory canal of C. elegans, (b) deletions, additions and substitutions of (a) which direct expression of a heterologous nucleic acid to the excretory canal of C. elegans, and (c) complements of (a) or (b) which direct expression of a heterologous nucleic acid to the excretory canal of C. elegans.

According to another aspect of the invention, an expression vector which is suitable for directing tissue-specific expression of a heterologous DNA fragment in the excretory cell of C. elegans is provided. The expression vector comprises a promoter, the promoter comprising a DNA fragment described above in the first aspect of the invention, positioned to direct expression of the heterologous DNA fragment. In one embodiment, the heterologous DNA fragment is a reporter gene. In certain embodiments, the reporter gene encodes green fluorescent protein, β-galactosidase, β-lactamase, luciferase, acetohydroxyacid synthase, alkaline phosphatase, β-glucuronidase, chloramphenicol acetyltransferase, horseradish peroxidase, nopaline synthase or octapine synthase.

According to another aspect of the invention, a host cell transformed or transfected with any of the foregoing expression vectors, is provided. In important embodiments, the host cell is a C. elegans cell.

According to still another aspect of the invention, a transgenic C. elegans containing a transgene comprising a promoter which is capable of directing tissue-specific gene expression in the excretory cell of C. elegans operatively linked to a protein-encoding DNA fragment is provided. Preferred DNA fragments comprising the promoter are as described above. In important embodiments, the protein-encoding DNA fragment comprises a reporter gene encoding green fluorescent protein, β-galactosidase, β-lactamase, luciferase, acetohydroxyacid synthase, alkaline phosphatase, β-glucuronidase, chloramphenicol acetyltransferase, horseradish peroxidase, nopaline synthase or octapine synthase. In certain embodiments, the transgene is stably integrated into a chromosome of the C. elegans. In some embodiments, the transgenic C. elegans further comprises a second transgene, wherein the second transgene comprises a promoter suitable for directing tissue-specific gene expression in the excretory cell of C. elegans operatively linked to a reporter gene. Preferred promoters of the second transgene are the same as those for the first transgene. Preferred reporter genes are also as described above. In further embodiments, one or both of the transgenes may be integrated into a chromosome of the C. elegans.

According to another aspect of the invention, a method of identifying a mutation in a gene involved in growth cone steering, cell motility, cell shape, tumor formation, tumor metastasis, vascularisation of tumors, renal development, kidney disease, the development of the excretory canal, cytoskeletal organisation or surface to cytoskeleton signalling, is provided. The method involves contacting a transgenic C. elegans which expresses a reporter gene in the excretory canal with a mutagen, and screening for phenotypic changes in the excretory canal. In some embodiments, the mutagen is EMS, UV-TMP or X-rays. Preferred transgenic C. elegans are as described above. The transgenic C. elegans may be a wild-type strain or a selected mutant strain.

According to yet another aspect of the invention, a method of determining whether a compound is an inhibitor or an enhancer of the regulation of growth cone steering, cell motility, cell shape, tumor formation, tumor metastasis, vascularisation of tumors, renal development, pathways involved in kidney disease, development of the excretory canal, cytoskeletal organisation or surface to cytoskeleton signalling, is provided. The method involves contacting a sample of the compound with a transgenic C. elegans which expresses a reporter gene in the excretory canal, and screening for phenotypic changes in the excretory canal. Preferred transgenic C. elegans are as described in any of the foregoing aspects of the invention.

According to another aspect of the invention, a compound which is identifiable as an inhibitor or an enhancer of the regulation of growth cone steering, cell motility, cell shape, tumor formation, tumor metastasis, vascularisation of tumors, renal development, pathways involved in kidney disease, development of the excretory canal, cytoskeletal organisation or surface to cytoskeleton signalling using the method of the invention described above in the immediately preceding paragraph, is provided. In certain embodiments, the compound is used as a medicament for promoting neuronal regeneration, re-vascularisation or wound healing. In some embodiments, the compound is used as a medicament for the treatment of chronic neuro-degenerative diseases, tumor formation, tumor metastasis, tumor vascularisation, kidney diseases, kidney cyst formation, polycystic kidney diseases, cell migration diseases or immunological diseases. In further embodiments, the compound is used to prepare a pharmaceutical composition. The pharmaceutical composition provided according to the invention, therefore, comprises the compound and a pharmaceutically acceptable carrier, diluent or excipient thereof.

According to still another aspect of the invention, a method of determining the function of a protein encoded by a DNA fragment, is provided. The method involves (a) providing a transgenic C. elegans containing a transgene comprising a promoter suitable for directing tissue-specific gene expression in the C. elegans excretory cell operatively linked to a protein encoded by a DNA fragment, and (b) observing any phenotypic changes in the excretory canal of the transgenic C. elegans. Preferred promoter sequnces, reporter genes, transgenes and transgenic C. elegans, are as described above.

According to still a further aspect of the invention, a method of determining whether a compound is a modulator of growth cone steering, cell shape, tumor formation, tumor metastasis, vascularisation of tumors, cell motility, renal development, a pathway involved in kidney disease, development of the excretory canal, cytoskeletal organisation or surface to cytoskeleton signalling, is provided. The method involves (a) contacting a sample of the compound with a transgenic C. elegans expressing a DNA fragment encoding a protein involved in the regulation of growth cone steering, cell shape, cell motility, renal development or a pathway involved in kidney disease, which transgenic C. elegans contains a transgene comprising a promoter which is suitable for directing tissue-specific gene expression in the C. elegans excretory cell operatively linked to the DNA fragment; and (b) screening for phenotypic changes in the excretory canal. Preferred promoter sequnces, reporter genes, transgenes and transgenic C. elegans, are as described above. In important embodiments, the transgenic C. elegans has an abnormal excretory canal phenotype. In certain embodiments the DNA fragment expressed in the excretory cell of the transgenic C. elegans rescues an abnormal excretory canal phenotype which is present in the genetic background of the transgenic C. elegans.

According to another aspect of the invention, a compound which is identifiable as a modulator of growth cone steering, cell shape, cell motility, tumor formation, tumor metastasis, vascularisation of tumors, renal development, a pathway involved in kidney disease, development of the excretory canal, cytoskeletal organisation or surface to cytoskeleton signalling using the method described above in the immediately preceding paragraph, is provided. In certain embodiments, the compound is used as a medicament for promoting neuronal regeneration, re-vascularisation or wound healing. In some embodiments, the compound is used as a medicament for the treatment of chronic neuro-degenerative diseases, tumor metastasis, tumor formation, tumor vascularisation, kidney diseases, kidney cyst formation, polycystic kidney diseases, cell migration diseases or immunological diseases.

According to still a further aspect of the invention, a pharmaceutical composition comprising a compound as described in the immediately preceding paragraph, and a pharmaceutically acceptable carrier, diluent or excipient thereof, is provided.

According to yet another aspect of the invention, a method of identifying further components of a biochemical pathway on which a compound identifiable as a modulator of growth cone steering, cell shape, cell motility, renal development, a pathway involved in kidney disease, development of the excretory canal, cytoskeletal organisation or surface to cytoskeleton signalling may act, is provided. The method involves (a) providing a transgenic C. elegans which expresses a reporter gene in the excretory canal, (b) contacting the transgenic C. elegans with a mutagen, (c) contacting the mutated C. elegans with a compound which is identifiable as a modulator of growth cone steering, cell shape, cell motility, renal development, a pathway involved in kidney disease, development of the excretory canal, cytoskeletal organisation or surface to cytoskeleton signalling, and (d) screening for phenotypic changes in the excretory canal. Preferred mutagens, promoter sequnces, reporter genes, transgenes and transgenic C. elegans, are as described above.

These and other aspects of the invention, as well as various advantages and utilities, will be more apparent with reference to the drawings and detailed description of the preferred embodiments.

BRIEF DESCRIPTION OF THE SEQUENCES

Figure 1:
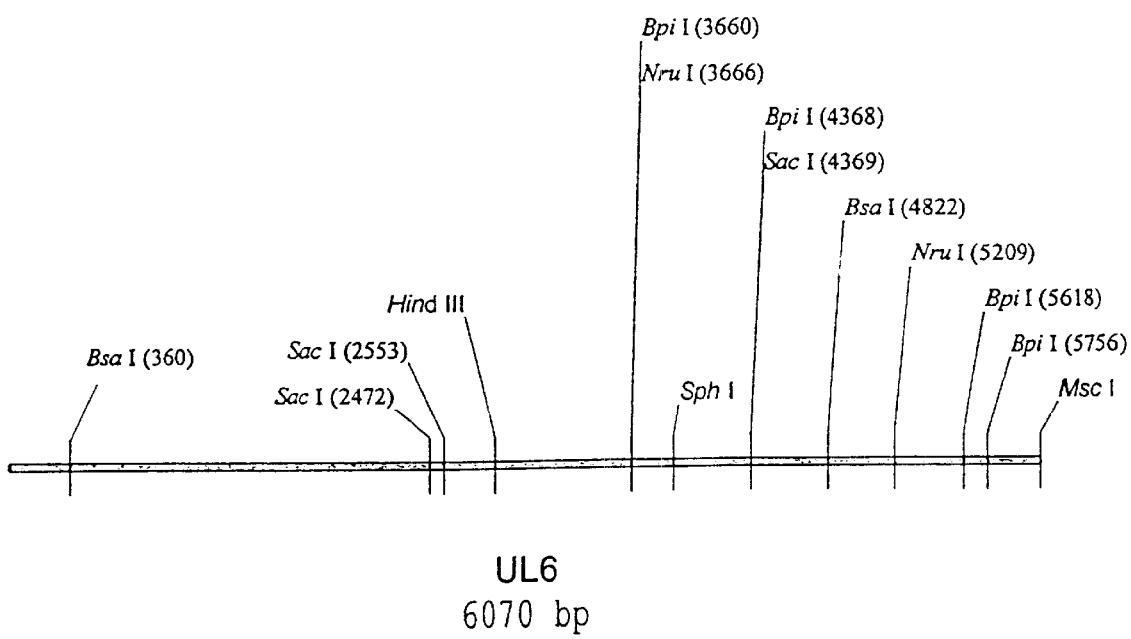
FIG. 1 shows a restriction map of the UL6 fragment.
Figure 2:
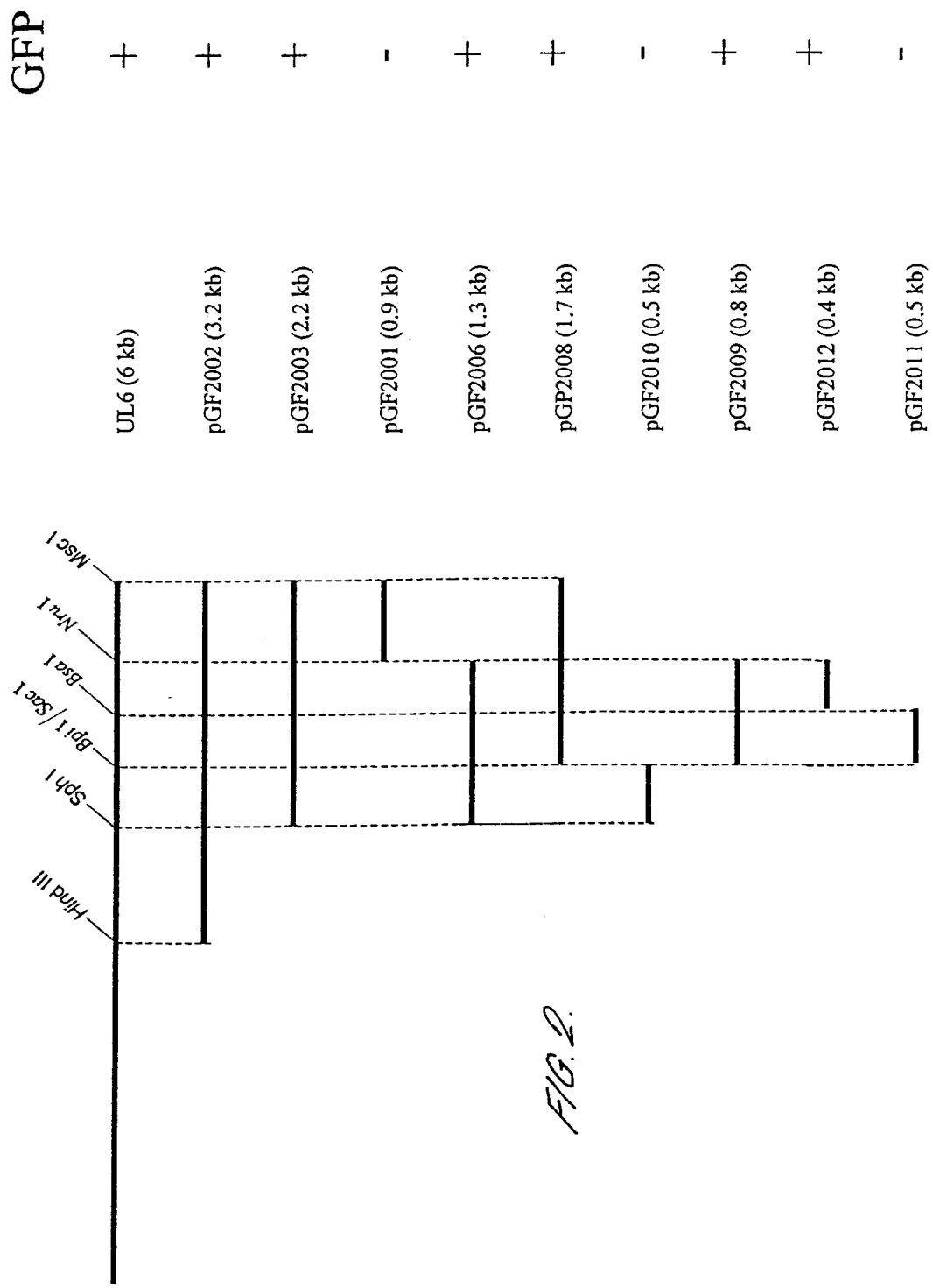
FIG. 2 is an overview of the series of plasmids containing deletion fragments of UL6.
Figure 3:
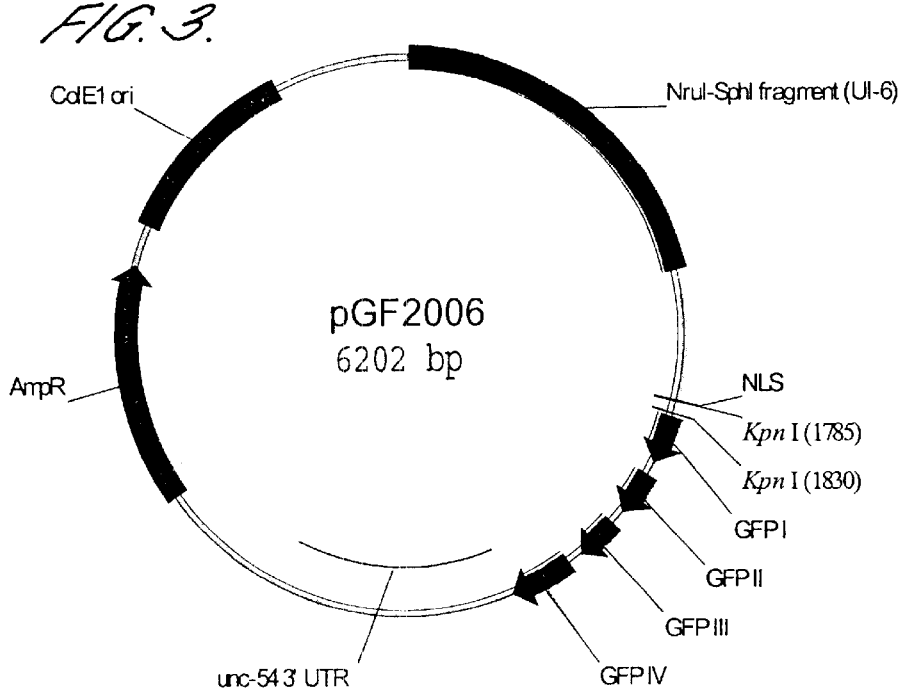
FIG. 3 is a plasmid map of pGF2006.
Figure 4:
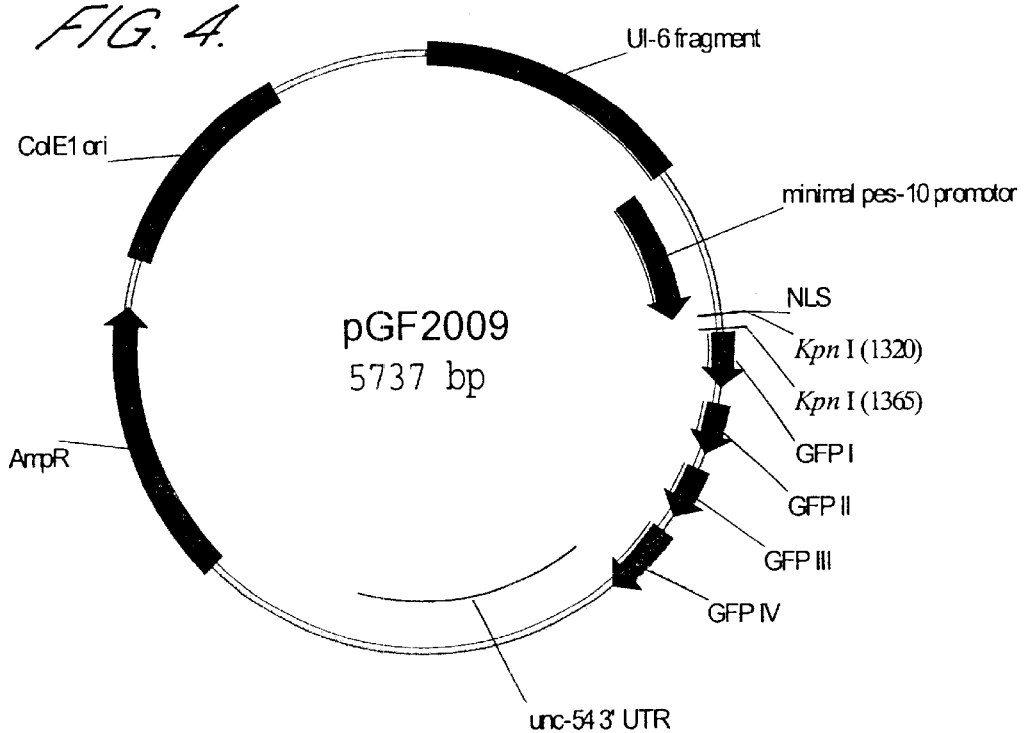
FIG. 4 is a plasmid map of pGF2009.
Figure 5:
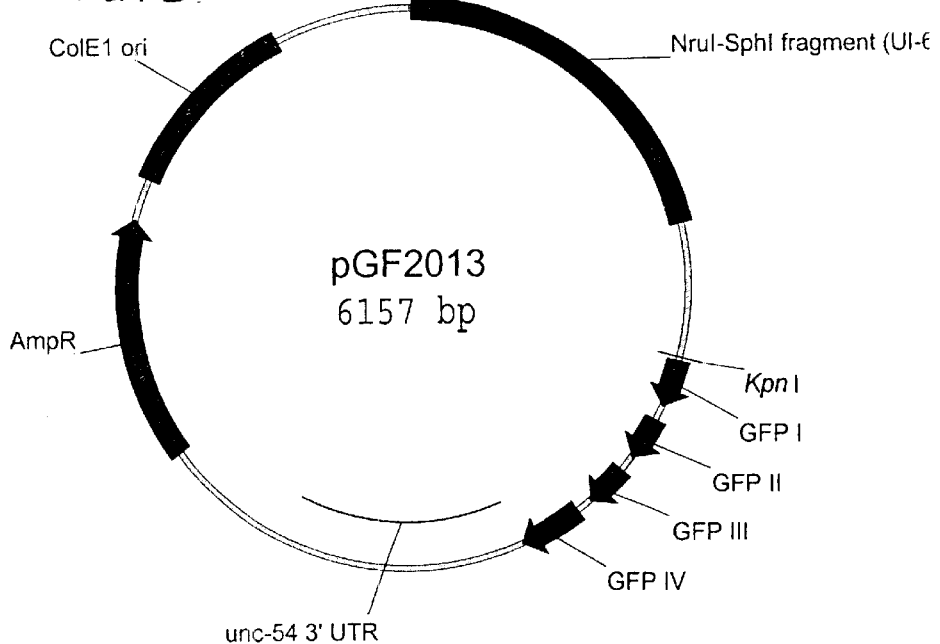
FIG. 5 is a plasmid map of pGF2013.
Figure 6:
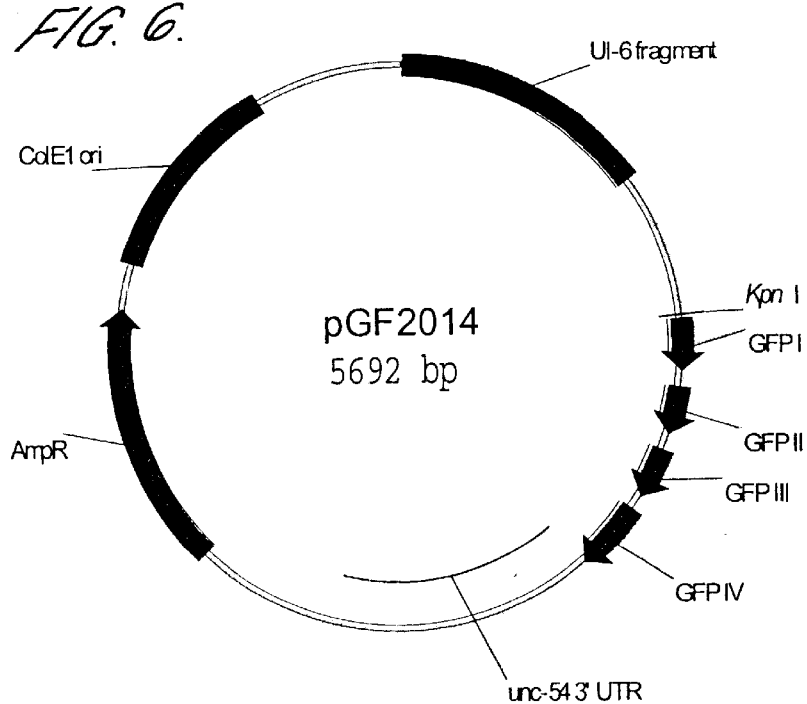
FIG. 6 is a plasmid map of pGF2014.

SEQ ID NO: 1 is the nucleic acid sequence of the insert of pUL6#64A1.

SEQ ID NO:2 is the nucleic acid sequence of the insert of pGF2002.

SEQ ID NO:3 is the nucleic acid sequence of the insert of pGF2003.

SEQ ID NO:4 is the nucleic acid sequence of the insert of pGF2006.

SEQ ID NO:5 is the nucleic acid sequence of the insert of pGF2008.

SEQ ID NO:6 is the nucleic acid sequence of the insert of pGF2009.

SEQ ID NO:7 is the nucleic acid sequence of the insert of pGF2012.

DETAILED DESCRIPTION OF THE INVENTION

DNA fragments having the nucleotide sequences set forth in SEQ ID NOs:2 to 7 exhibit tissue-specific promoter activity, directing transcription specifically in the excretory cell and excretory canal of C. elegans. That is to say when a reporter gene under the control of any one of these DNA fragments is introduced into C. elegans a high level of reporter gene expression is observed in the excretory cell and excretory canal with only background expression in other tissues. As will be described below, these tissue-specific promoters are useful tools in the construction of expression vectors which are suitable for directing gene expression specifically in the C. elegans excretory cell and excretory canal and in the construction of transgenic C. elegans in which the transgene is expressed specifically in the excretory cell and excretory canal.

In the context of the present application, the phrase "in the absence of any further sequence of consecutive nucleotides from the C. elegans genome" should be interpreted as meaning in the absence of any other C. elegans genomic sequence consecutive with the sequences shown in SEQ ID NOs:2 to 7, respectively. In other words, the DNA fragments of the invention preferably contain the sequences shown in SEQ ID NOs:2 to 7 in the absence of any other consecutive UL6 promoter sequences and can be considered isolated.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not.

An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

According to another aspect of the invention, an isolated nucleic acid molecule, is provided. The isolated nucleic acid molecule can comprise: (a) nucleic acid molecules which hybridize under stringent conditions to a molecule consisting of a nucleic acid having a sequence selected from the group consisting of SEQ ID NO:2, SEQ ID NO:3, SEQ ID NO:4, SEQ ID NO:5, SEQ ID NO:6, and SEQ ID NO:7, and which direct expression of a heterologous DNA fragment to the excretory canal of C. elegans, (b) deletions, additions and substitutions of (a) which direct expression of a heterologous nucleic acid to the excretory canal of C. elegans, and (c) complements of (a) or (b) which direct expression of a heterologous nucleic acid to the excretory canal of C. elegans.

The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrolidone, 0.02% Bovine Serum Albumin, 2.5 mM $NaH_2PO_4$(pH7), 0.5% SDS, 2mM EDTA). SSC is 0.15M sodium chloride/0.15M sodium citrate, pH7; SDS is sodium dodecyl sulphate; and EDTA is ethylenediaminetetracetic acid. After hybridization, the membrane upon which the DNA is transferred is washed at 2×SSC at room temperature and then at 0.1×SSC/0.1×SDS at temperatures up to 68° C.

There are other conditions, reagents, and so forth which can be used, and would result in a similar degree of stringency. The skilled artisan will be familiar with such conditions, and thus they are not given here.

In another aspect the invention provides an expression vector which is suitable for directing tissue-specific expression of a heterologous DNA fragment in the excretory cell of C. elegans, the vector comprising a promoter comprising a DNA fragment as set forth in any one of SEQ ID NOs:2 to 7 positioned to direct expression of the heterologous DNA fragment.

The term "heterologous DNA fragment" refers to essentially any DNA fragment which it is desired to express in the excretory cell of C. elegans. This DNA fragment can be a gene, a cDNA or a fragment thereof from C. elegans, Drosophila sp., mouse, human, zebrafish or any other invertebrate or vertebrate origin. Alternatively, the DNA fragment may be of prokaryotic origin, a recombinant DNA or a synthetic DNA fragment. In a preferred embodiment the heterologous DNA is a reporter gene. Suitable reporter genes include those encoding green fluorescent protein (including the many GFP variants and equivalents known in the art), β-galactosidase, β-lactamase, luciferase, acetohydroxyacid synthase, alkaline phosphatase, β-glucuronidase, chloramphenicol acetyltransferase, horseradish peroxidase, nopaline synthase or octapine synthase. The above are listed by way of example only and it is to be understood that the precise nature of the heterologous DNA fragment is not material to the invention.

In order to achieve expression in eukaryotic host cells (e.g. cells of the nematode worm C. elegans) an expression vector must include promoter sequences to position RNA polymerase at the transcription start site and to direct an appropriate frequency of transcription initiation at this site (e.g. to direct tissue-specific expression in the C. elegans excretory cell). In accordance with the invention, the promoter region of the expression vector may comprise UL6 promoter sequences which fulfil both functions (i.e. which contain the transcription initiation site for binding of RNA polymerase and which direct tissue-specific expression) or the promoter region of the vector may comprise a minimal promoter region from an heterologous gene (e.g. the pes-10 promoter) which functions to position RNA polymerase at the transcription initiation site and possibly to direct a basal level of transcription and UL6 promoter sequences to direct a tissue-specific expression pattern. This will be further understood with reference to the accompanying Examples. The vector might further comprise one or more additional transcriptional regulatory elements (e.g. enhancer elements) in addition to the UL6 promoter sequences.

The expression vector may also include the following elements required for eukaryotic gene expression: a terminator sequence and downstream polyadenylation signal for transcription termination, translation initiation sequences for ribosome binding, a start codon (usually AUG) and a termination codon for detachment of the ribosome. Such vectors may be obtained commercially or may be assembled from the elements described by methods well known in the art.

Examples of expression vectors according to the invention are plasmids, viral or phage vectors, plasmid vectors being preferred for use in C. elegans. Such vectors will normally possess one or more selectable markers, such as a gene for antibiotic resistance. Plasmid vectors, including those designed for expression in C. elegans, may also contain a bacterial origin of replication to allow replication in bacterial host cells for cloning purposes. The construction of plasmid vectors suitable for directing expression of a reporter gene in the excretory cell of C. elegans are described in detail in the accompanying Examples.

Also provided by the invention are host cells and organisms transformed or transfected with the expression vector.

In a still further aspect the invention provides a transgenic C. elegans containing a transgene comprising a promoter which is capable of directing tissue-specific gene expression in the excretory cell of C. elegans operatively linked to a protein-encoding DNA fragment.

According to the invention the transgene may comprise any promoter which is capable of directing tissue-specific gene expression in the excretory cell of C. elegans operatively linked to any DNA fragment which it is desired to express in the excretory cell and excretory canal of C. elegans. Where a promoter is described herein as being capable of or suitable for directing tissue-specific gene expression in the excretory cell and/or excretory canal this should be taken to mean that the promoter directs a relatively high level of expression in the excretory cell and/or excretory canal and only background expression in other tissues. In a preferred embodiment the promoter comprises a DNA fragment, as described above, comprising a sequence of nucleotides as set forth in any one of SEQ ID NOs:2 to 7 in the absence of any other consecutive sequence of nucleotides from the C. elegans genome, i.e. in the absence of any consecutive UL6 promoter sequences. The promoter may, if appropriate, contain sequences from elsewhere in the C. elegans genome which are not consecutive with the sequences shown in SEQ ID NOs:2 to 7, for example one or more further cis-acting regulatory elements isolated from a different type of promoter.

In this context the term "transgene" refers to a DNA construct comprising a promoter operatively linked to a protein-encoding DNA fragment. The construct may contain additional DNA sequences in addition to those specified above. The transgene may, for example, form part of a plasmid vector. By the term "operatively linked" it is to be understood that the promoter is positioned to drive transcription of the protein-encoding DNA fragment.

A transgenic C. elegans according to this aspect of the invention may be constructed according to any of the standard techniques known to those skilled in the art. A suitable approach involves the construction of a plasmid-based expression vector in which a protein-encoding DNA of interest is cloned downstream of a promoter capable of directing tissue-specific gene expression in the excretory cell of C. elegans. The plasmid vector is then injected into N2 nematodes. In order to facilitate the selection of transgenic nematodes a second plasmid carrying a dominant selectable marker may be co-injected with the experimental plasmid.

The plasmid vector is maintained in cells of the transgenic C. elegans in the form of an extrachromosomal array. Although plasmid vectors are relatively stable as extrachromosomal arrays they can alternatively be stably integrated into the C. elegans genome using standard technology, for example, using gamma ray-induced integration of extrachromosomal arrays (methods in Cell Biology, Vol 48 page 425–480).

The protein-encoding DNA fragment can be any DNA fragment which it is desired to express in the excretory canal of C. elegans. This DNA fragment can be a gene, a cDNA or a fragment thereof from C. elegans, Drosophila sp., mouse, human, zebrafish or any other invertebrate or vertebrate origin. Alternatively, the DNA fragment may be of prokaryotic origin, a recombinant DNA or a synthetic DNA fragment.

In a preferred embodiment the DNA fragment is a promoterless reporter gene encoding a marker protein such as, for example, green fluorescent protein (GFP), β-galactosidase, β-lactamase, luciferase, acetohydroxyacid synthase, alkaline phosphatase, β-glucuronidase, chloramphenicol acetyltransferase, horseradish peroxidase, nopaline synthase or octapine synthase. The expression of a marker such as GFP makes it possible to visualize the excretory cell in situ in the body of the worm without intervening biochemical steps or specialized equipment such as nomarski-microscopy. A GFP-expressing excretory cell can be readily visualized using binocular microscopy following UV irradiation of the worm.

According to the invention, the transgenic C. elegans can be of any genetic background, for example, it can be a wild type worm, a selected mutant worm or a transgenic worm. A stably integrated transgene can easily be transferred onto a different genetic background by performing a genetic cross between a first parental C. elegans strain containing a stably integrated transgene and a second parental C. elegans strain of the desired genetic background. Standard C. elegans genetics can be employed for this purpose. The genetic background of the worm generally has no effect on the expression of the transgene in the excretory cell and excretory canal.

In a further embodiment of the invention the transgenic C. elegans further comprises a second transgene comprising a promoter which is suitable for directing tissue-specific expression in the excretory cell of C. elegans operatively linked to a reporter gene.

This "double transgenic" C. elegans can be constructed by co-injecting C. elegans with two plasmid expression vectors; one containing the protein-encoding DNA fragment of interest and the other containing a reporter gene following the procedure described above. Both of the plasmid vectors can be stably integrated into the C. elegans genome using standard techniques (methods in Cell Biology, Vol 48 page 425–480).

In a further aspect the invention provides a method of identifying a mutation in a gene involved in growth cone steering, cell motility, cell shape, tumor formation, tumor metastasis, vascularisation of tumors, the development of the excretory canal, cytoskeletal organisation, surface to cytoskeleton signalling, renal development or kidney disease, which method comprises contacting a transgenic C. elegans which expresses a reporter gene in the excretory canal with a mutagen and screening for phenotypic changes in the excretory canal.

Suitable mutagens for use in the method of the invention include EMS, X-rays or the UV-TMP method, all of which are known to those skilled in the art. Following contact with mutagen the transgenic C. elegans are maintained in culture for at least two subsequent generations during which time observations of the morphology of the excretory canals of the progeny are made in order to identify any mutants with an abnormal excretory canal phenotype. Suitable culture conditions are described in the examples given herein.

The expression of a reporter gene such as GFP in the excretory canal allows mutations that affect the development, shape, growth direction and outgrowth of the excretory canal to be observed and selected. The affected gene is then isolated and characterized using standard genetic and molecular biology techniques.

In a preferred embodiment of the method of the invention the transgenic C. elegans which express a reporter gene in the excretory canal contains a transgene comprising a promoter which is suitable for directing tissue-specific gene expression in the excretory canal of C. elegans operatively linked to a reporter gene. The promoter preferably comprises a DNA fragment having the sequence of nucleotides set forth in any one of SEQ ID NOs:2 to 7.

The method of the invention may also be adapted for use in the identifying further components of a biochemical pathway involved in growth cone steering, cell motility, cell shape, tumor formation, tumor metastasis, vascularisation of tumors, the development of the excretory canal, cytoskeletal organisation, surface to cytoskeleton signalling, renal development or kidney disease. In this case the mutagenesis method as described above is performed on a transgenic C. elegans expressing a reporter gene in the excretory cell whose genetic background is a selected mutant strain. The selected mutant strain is a strain carrying a defined mutation in a gene involved in growth cone steering, cell motility, cell shape, tumor formation, tumor metastasis, vascularisation of tumors, the development of the excretory canal, cytoskeletal organisation, surface to cytoskeleton signalling, renal development or kidney disease.

The selected mutant strain may be the result of a previous round of random mutagenesis performed on a wild-type C. elegans strain or it may be a known mutant strain, for example a knock-out mutant or an over-expressing strain taken from a *C. elegans* collection (e.g. the *C. elegans* mutant collection at the *C. elegans* Genetic Center, University of Minnesota, St Paul, Minn., USA). Methods for creating mutant worms with mutations in selected *C. elegans* genes are known in the art, for example see J. Sutton and J. Hodgkin in "*The Nematode Caenorhabditis elegans*" Ed. by William B. Wood and the Community of *C. elegans* Researchers CSHL, 1988 594–595; Zwaal et al. "Target-Selected Gene Inactivation in *Caenorhabditis elegans* by using a Frozen Transposon Insertion Mutant Bank" 1993, Proc. Natl. Acad. Sci. USA 90 pp7431–7435; Fire et al. "Potent and Specific Genetic Interference by Double-Stranded RNA in *Caenorhabditis elegans*" 1998, Nature 391 860–811.

Further treatment of a selected mutant strain with mutagen results in the production of a double mutant but it is the phenotype of the later mutation (i.e. that resulting from contact with mutagen) which is scored by screening the subsequent generation for further morphological changes in the excretory canal. If the phenotype of the selected mutant is enhanced in the progeny after mutagenesis this indicates that the second mutation has occurred in a gene which acts on the same or a parallel biochemical pathway to the gene affected by the defined mutation. Alternatively, if the phenotype of the selected mutant is suppressed in the double-mutant progeny this indicates that the second mutation event has occurred in an important gene in the biochemical pathway.

Transgenic *C. elegans* for use in this method, or for use in any of the subsequently described methods which require the use of transgenic *C. elegans* expressing protein encoding DNAs and/or reporter genes in the excretory cell and excretory canal, may be constructed according to standard techniques known in the art such as the methodology described by Craig Mello and Andrew Fire, Methods in Cell Biology, Vol 48 Ed. H. F. Epstein and D. C. Shakes, Academic Press, pages 452–480.

The present invention further provides a method of determining whether a compound is an inhibitor or an enhancer of the regulation of growth cone steering, cell motility, cell shape, tumor formation, tumor metastasis, vascularisation of tumors, renal development, pathways involved in kidney disease, development of the excretory canal, cytoskeletal organisation or surface to cytoskeleton signalling, which method comprises contacting a sample of the compound with a transgenic *C. elegans* expressing a reporter gene in the excretory canal and screening for phenotypic changes in the excretory canal.

Contact with a compound which is an inhibitor or an enhancer of the regulation of growth cone steering, cell motility, cell shape, tumor formation, tumor metastasis, vascularisation of tumors, renal development, pathways involved in kidney disease, development of the excretory canal, cytoskeletal organisation or surface to cytoskeleton signalling results in changes the morphology of the excretory canal. The expression of a reporter gene in the excretory canal allows these changes in morphology to be easily visualized. Commonly observed abnormal excretory canal morphologies include: nematodes having shorter or longer canals, nematodes having curved or extra branched canals, nematodes having ventral or dorsal canals, nematodes having more or less than two canals, nematodes having wrongly branched canals, nematodes having vacuoles or cysts, nematodes with unusual features in the excretory canal.

Preferred reporter genes include those encoding green fluorescent protein, β-galactosidase, β-lactamase, luciferase, acetohydroxyacid synthase, alkaline phosphatase, β-glucuronidase, chloramphenicol acetyltransfersae, horseradish peroxidase, nopaline synthase or octapine synthase. In a preferred embodiment the transgenic *C. elegans* which express a reporter gene in the excretory canal contains a transgene comprising a promoter which is suitable for directing tissue-specific gene expression in the excretory canal of *C. elegans* operatively linked to a reporter gene. The promoter preferably comprises a DNA fragment having the sequence of nucleotides set forth in any one of SEQ ID NOs:2 to 7. The genetic background of the transgenic worm can be wild-type, alternatively the worm can be a mutated worm or a worm expressing a second transgene.

For the avoidance of doubt, it is hereby stated that although the above-described method, and similar screening methods described hereinbelow, are based on bringing *C. elegans* worms into contact with compounds which may potentially have useful pharmacological activity there is no intention to provide any therapeutic benefit to the *C. elegans* during the screen. The worms are used merely as a tool to find out something about the properties of a compound in a biological system. In principle, this is similar to carrying out compound screening in vitro using mammalian cells except that the biological system is a microscopic multicellular organism rather than a single cell.

It will be appreciated that a wide variety of candidate compounds may be tested using the screening methods described herein. The compound may be of any chemical formula and may be one of known biological or pharmacological activity, a known compound without such activity or a novel molecule such as might be present in a combinatorial library of compounds.

The invention further provides a compound which is identifiable using the above method as an inhibitor or an enhancer of the regulation of growth cone steering, cell motility, cell shape, tumor formation, tumor metastasis, vascularisation of tumors, renal development, pathways involved in kidney diseases, development of the excretory canal, cytoskeletal organisation or surface to cytoskeleton signalling.

The invention also provides use of this compound as a medicament, or in the manufacture of a medicament, for promoting neuronal regeneration, re-vascularisation or wound healing or for the treatment of chronic neuro-degenerative diseases, tumor formation, tumor metastasis, tumor vascularisation, kidney diseases, polycystic kidney diseases (specifically ADPKD), cell migration diseases or immunological diseases. Also provided by the invention is a pharmaceutical composition comprising the compound plus a pharmaceutically acceptable carrier, diluent or excipient.

The present invention further provides a method of determining the function of the protein encoded by a DNA fragment, which method comprises the steps of:

(a) providing a transgenic *C. elegans* containing a transgene comprising a promoter which is suitable for directing tissue-specific gene expression in the *C. elegans* excretory cell operatively linked to the DNA fragment; and (b) observing any phenotypic changes in the excretory canal of the transgenic *C. elegans*.

According to the method of the invention the function of a given protein or peptide may be studied by expressing the protein in the excretory canal of *C. elegans*. Analysis of any resultant phenotypic changes in the excretory canal may result in a better understanding of the function of the protein.

The transgene comprises a promoter which directs transcription specifically in the *C. elegans* excretory cell and excretory canal. The DNA fragment encoding the protein of interest, which DNA fragment may be a genomic DNA, a cDNA or a fragment thereof, is placed under the control of this promoter and thereby expressed specifically in the excretory cell and excretory canal. In a preferred embodiment the promoter comprises a DNA fragment having the sequence of nucleotides set forth in any one of SEQ ID NOs:2 to 7.

In order to help visualise any phenotypic changes in the excretory canal the transgenic *C. elegans* may further comprise a second transgene comprising a promoter suitable for directing tissue-specific gene expression in the *C. elegans* excretory cell operatively linked to a reporter gene, preferably green fluorescent protein, β-galactosidase, β-lactamase, luciferase, acetohydroxyacid synthase, alkaline phosphatase, β-glucuronidase, chloramphenicol acetyltransferase, horseradish peroxidase, nopaline synthase or octapine synthase. As described above, expression of a reporter gene such as GFP makes it possible to visualise the excretory canal without the need for specialized equipment.

If expression of a given protein in the excretory cell results in an abnormal excretory canal phenotype then in a further embodiment the method of the invention may be combined with a mutagenesis step in order to identify further components of the biochemical pathway on which the protein acts. In this embodiment a transgenic *C. elegans* expressing the protein in the excretory canal is contacted with a mutagen, for example, EMS, UV-TMP or X-rays, all of which are well known in the art, and then maintained in culture for at least two subsequent generations during which time the morphology of the excretory canal is observed. If contact with mutagen results in either enhancement or suppression of the abnormal excretory canal phenotype then this indicates that a mutation has occurred in a gene encoding a component of the same biochemical pathway to that on which the original protein acts or of a parallel biochemical pathway. The mutated gene can then be isolated and characterised using standard molecular biology and biochemical techniques.

The invention further provides a method of determining whether a compound is a modulator of growth cone steering, cell shape, cell motility, tumor formation, tumor metastasis, vascularisation of tumors, renal development, a pathway involved in kidney disease, development of the excretory canal, cytoskeletal organisation or surface to cytoskeleton signalling, which method comprises the steps of;

a) contacting a sample of the compound with a transgenic *C. elegans* expressing a DNA fragment encoding a protein involved in the regulation of growth cone steering, cell shape, cell motility, renal development or a pathway involved in kidney disease, which transgenic *C. elegans* contains a transgene comprising a promoter which is suitable for directing tissue-specific gene expression in the *C. elegans* excretory cell operatively linked to the DNA fragment; and (b) screening for phenotypic changes in the excretory canal.

The transgenic *C. elegans* may be a wild type strain or a selected mutant strain. In one embodiment the transgenic worm has an abnormal excretory canal phenotype. Alternatively, the DNA fragment expressed in the excretory cell of the transgenic worm rescues an abnormal excretory canal phenotype which is present in the genetic background of the transgenic *C. elegans*.

Visible phenotypic changes in excretory canal morphology may include: nematodes having shorter or longer canals, nematodes having curved or extra branched canals, nematodes having ventral or dorsal canals, nematodes having more or less than two canals, nematodes having wrongly branched canals, nematodes having vacuoles or cysts, nematodes with unusual features in the excretory canal. To assist in visualising any phenotypic changes the transgenic worm may further express a reporter gene, preferably encoding green fluorescent protein, in the excretory canal.

The present invention further provides a compound which is identifiable as a modulator of growth cone steering, cell shape, cell motility, renal development, a pathway involved in kidney disease, development of the excretory canal, cytoskeletal organisation or surface to cytoskeleton signalling according to the above method. The invention also provides use of this compound as a medicament, or in the manufacture of a medicament, for promoting neuronal regeneration, re-vascularisation or wound healing, or for the treatment of chronic neuro-degenerative diseases, tumor metastasis, kidney diseases, kidney cyst formation, polycystic kidney diseases (specifically ADPKD), cell migration diseases or immunological diseases. The compound may be provided as a pharmaceutical composition comprising the compound and a pharmaceutically acceptable carrier, diluent or excipient.

In a still further aspect the invention provides a method of identifying further components of a biochemical pathway on which a compound identifiable as a modulator of growth cone steering, cell shape, tumor formation, tumor metastasis, vascularisation of tumors, cell motility, renal development, a pathway involved in kidney disease, development of the excretory canal, cytoskeletal organisation or surface to cytoskeleton signalling may act, which method comprises the steps of:

(a) providing a transgenic *C. elegans* which expresses a reporter gene in the excretory canal;

(b) contacting the transgenic *C. elegans* with a mutagen;

(c) contacting the mutated *C. elegans* with a compound which is identifiable as a modulator of growth cone steering, cell shape, tumor formation, tumor metastasis, vascularisation of tumors, cell motility, renal development, a pathway involved in kidney disease, development of the excretory canal, cytoskeletal organisation or surface to cytoskeleton signalling; and (d) screening for phenotypic changes in the excretory canal.

Following contact with mutagen and the compound the transgenic *C. elegans* are maintained in culture for at least two subsequent generations during which time observations of the morphology of the excretory canals of the progeny are made in order to identify any changes in excretory canal phenotype. As with the other screening methods hereinbefore described the expression of a reporter gene, such as GFP, makes it easy to visualise any phenotypic changes in the excretory canal.

The compound used in this method is one which is identifiable as a modulator of growth cone steering, cell shape, tumor formation, tumor metastasis, vascularisation of tumors, cell motility, renal development, a pathway involved in kidney disease, development of the excretory canal, cytoskeletal organisation or surface to cytoskeleton signalling using one of the methods hereinbefore described for that purpose. As described above, treatment of *C. elegans* with such a compound produces morphological abnormalities in the excretory canal. Suitable mutagens for use in the method of the invention include EMS, X-rays or the UV-TMP method, all of which are known to those skilled in the art.

The use of mutagenesis in the method of the invention facilitates the identification of further components of the biochemical pathway on which the compound acts. If the mutagenesis step results in the production of mutant progeny in which the abnormal excretory canal phenotype is enhanced (as compared with the phenotype observed following treatment of non-mutated *C. elegans* with the same compound) then the mutation has occurred in a gene in the same biochemical pathway as that on which the compound acts or a parallel pathway. Alternatively, treatment of *C. elegans* according to the method results in mutant progeny in which the abnormal excretory canal phenotype is suppressed, indicating that a mutation has occurred in a gene having an important function on the biochemical pathway on which the compound acts. In either case the gene affected by the mutation can be isolated and characterised using standard molecular biology and biochemical techniques.

In a preferred embodiment of the method of the invention the transgenic *C. elegans* which express a reporter gene in the excretory canal contains a transgene comprising a promoter which is suitable for directing tissue-specific gene expression in the excretory canal of *C. elegans* operatively linked to a reporter gene. The promoter preferably comprises a DNA fragment having the sequence of nucleotides set forth in any one of SEQ ID NOs:2 to 7. The genetic background of the transgenic *C. elegans* may be wild type or it may be a selected mutant strain.

The invention will be more fully understood by reference to the following examples. These examples, however, are merely intended to illustrate the embodiments of the invention and are not to be construed to limit the scope of the invention.

EXAMPLES

General Experimental Methods

Sequence information and expression patterns were obtained from the *C. elegans* genome project, the Sanger Centre, and Washington University School of Medicine (Science, 282(5396):2011–2046 (1998)).

All Molecular biology work was performed using standard techniques known in the art, as described by Sambrook et al. (1989), *Molecular Cloning: A Laboratory Manual*, Cold Spring Harbor Laboratory Press; F. M. Ausubel et al. (eds.) or *Current Protocols in Molecular Biology*, John Wiley & Sons, Inc. (1994), or using minor modifications of the methods described therein.

All manipulations of *C. elegans* worms were performed using techniques described in Methods in Cell Biology, vol 84; *Caenorhabditis elegans:* modern biological analysis of an organism, ed. Epstein and Shakes, academic press, 1995, or using minor modifications of the methods described therein.

Transgenic *C. elegans* strains were constructed by injection of plasmid DNA into N2 worms using standard techniques known in the art (see Methods in Cell Biology, vol 84 as mentioned above). In order to facilitate the selection of transgenic strains the plasmid pRF4 (Mello, C. C. et al. EMBO J. 10, 3959–3970 (1991)) which carries the rol-6 gene was co-injected with the experimental plasmids as a marker. *C. elegans* expressing rol-6 exhibit the roller phenotype. Any other *C. elegans* dominant selectable phenotypic marker could be used in place of rol-6 with equivalent effect. When generating transgenic *C. elegans* strains with plasmids that encode for and express GFP or GFP fusion proteins, no co-injection with a dominant selective marker is needed, as the transgenic lines can be selected by simple isolation of the progeny that expresses GFP.

Example 1

GFP Expression in the Excretory Canal Using a Minimal Promoter Fragment pUL#64A1 was isolated as the result of a promoter trapping experiment described by Young J. M. and Hope I. A. Molecular markers of differentiation in *Caenorhabditis elegans* obtained by promoter trapping (1993) Dev. Dyn., 196:124–132. In this study partial Sau3AI restriction enzyme fragments of *C. elegans* genomic DNA were cloned in the BamHI restriction site of the vector pPD22.11 (described by Fire A, Harrison S. W., and Dixon D. A modular set of LacZ fusion vectors for studying gene expression in *Caenorhabditis elegans* (Gene 93:189–198 (1990)) creating LacZ translational fusions. Introduction of pUL#64A1 into *C. elegans* resulted in the expression of β-galactosidase in the excretory cell and excretory canal and the lateral nuclei of the hypodermis adjacent to the anterior and posterior of the excretory cell. The region of the genomic DNA insert immediately adjacent to the lacZ gene was sequenced enabling the origin of the insert of pUL#64A1 to be localized on the *C. elegans* physical genome map.

In order to determine the length of the cloned insert the vector pUL#64A1 was digested with several restriction enzymes, including XhoI SalI, SphI and HindIII. Restriction fragment length analysis showed that the cloned fragment in pUL#64A1 was approximately 6 kb in length. Analysis of the genomic DNA of *C. elegans* (available from the *C. elegans* genome project, the Sanger Centre, and Washington University School of Medicine (Science, 282(5396):2011–2046 (1998)) revealed the presence of two adjacent Sau3AI in the region of the pUL#64A1 insert (SEQ ID NO:1). This confirmed that the inserted DNA fragment had a length of 6065 bp or 6023 bp and could be located between positions 33561 and 39620 on cosmid C17H12. The inserted DNA fragment was designated UL6.

Analysis of the nucleotide sequence of the UL6 insert revealed the presence of two putative genes orientated in opposite directions. The putative promoter located upstream of the gene orientated in the same direction as the lacZ reporter gene was considered to be the most relevant for further analysis.

In order to test for promoter activity several deletion fragments of UL6 spanning this region were cloned in the GFP-fusion vector pPD95.79 (constructed by Andrew Fire, Carnegie Institute of Washington, (Gene 93:189–198 (1990)). The promoter activity of each of the fragments was then tested by injecting the plasmids into *C. elegans* and analysing the levels of GFP expression in different tissues.

A first construct, designated pGF2002, contained the 3.2 kb HindIII-MscI fragment of UL6. Following injection of pGF2002 into *C. elegans* worms, the F1 generation showed GFP expression in the head, tail, muscles and excretory canal, whilst the F2 generation (and subsequent generations) expressed GFP in the excretory canal with background expression in other cells. The background expression in the other cells is mosaic and depending from animal to animal the pharynx, the gut, muscle cells or the tail may show background GFP expression. The resulting strain was designated UG266 (bgEx34).

A smaller construct containing a 2.2 kb SphI-MscI fragment of UL6 in pPD95.79 was made and designated pGF2003. Following injection of pGF2003 into *C. elegans* worms, the F1 showed GFP expression in the head, tail, muscles and excretory canal, analogous to pGF2002. The expression of GFP in the F2 generation was not analysed but is expected to be analogous to that observed with pGF2002, i.e. strong expression in the excretory canal with background expression in other tissues.

Finally, a 0.9 kb NruI-MscI fragment of UL6 was cloned into pPD95.79 digested with MscI and XbaI, the later made blunt with Klenow polymerase. After injection of the resultant plasmid, designated pGF2001, into *C. elegans* no GFP expression could be observed.

These results and the fact that the excretory cell-specific promoter in the UL6 fragment was thought to be localized between the two genes, being approximately between the NruI and the SphI site, stimulated the inventors to analyse further deletion constructs. The aim was to determine the smallest fragment of UL6 that promotes the transcription and expression in the *C. elegans* excretory cell and excretory canal.

The 1.3 kb NruI-SphI insert of pGF2003 was excised and cloned into the vector pPD97.78. The latter vector is analogous to pPD95.79, but contains a minimal pes-10 promoter upstream of the GFP gene. This means that it is not necessary to make a fusion construct between the fragment to be tested for promoter activity and GFP. Vector pPD97.78 was digested with SphI and HindII and the resulting plasmid was designated pGF2006. Transgenic *C. elegans* animals harboring this plasmid from the F2 and subsequent generations show strong GFP expression in the excretory canal with only minor background expression in other cell types. The new *C. elegans* strain was designated UG267(bgEx35).

A 1.7 kb MscI-SacI fragment of pGF2003 was cloned in pPD95.79 and designated pGF2008. After injection of this plasmid into *C. elegans* worms the F1 generation showed GFP expression in the excretory canal, gut, head, tail and spermatheca.

The region that promotes the expression of GFP in the excretory canal seemed to be located in the 1.3 kb NruI-SphI insert of pGF2006. Further deletion analysis was therefore carried out to identify the minimal UL6 promoter in this fragment. Plasmid pGF2009 was generated by deleting a 0.5 kb BpiI-HindIII fragment of pGF2006, leaving a 0.9 kb fragment. The HindIII site is part of the multiple cloning site of the vector and adjacent to the SphI site. Plasmid pGF2010 was generated by deleting a 0.9 bp XbaI-BpiI fragment of pGF2006, leaving a 0.5 kb fragment. The XbaI site is part of the multiple cloning site of the vector and adjacent to the NruI-HindII fusion. The construction of this series of deletions will be further understood with reference to FIG. 8 which shows a restriction map of the UL6 insert and FIG. 9 which gives an overview of the UL6 deletion constructs.

*C. elegans* injected with pGF2009 showed GFP expression in the excretory canal, with only minor background expression in the other cells, analogous to the expression results with pGF2006. The resulting *C. elegans* strain was designated UG271 (bgEX38). No GFP could be detected in the F1 generation after introduction of pGF2010 into *C. elegans*.

Two further deletions have been constructed to define the minimal promoter capable of directing transcription in the excretory canal. pGF2009 was digested with restriction enzyme BsaI and made blunt with klenow polymerase. The resulting fragment was further digested with XbaI to give a 0.4 kb BsaI-XbaI fragment and with HindIII to give a 0.5 kb HindIII-BsaI fragment. These fragments were independently cloned in pPD97.78, using the HindIII-StuI and StuI-XbaI sites, respectively. The resulting vectors are designated pGF2011 and pGF2012. Injection of pGF2012 into *C. elegans* resulted in expression of GFP in the excretory canal.

Plasmid expression vectors suitable for expressing GFP or lacZ or any other reporter protein in the excretory canal of *C. elegans* can be integrated in the genome of the worm using standard technology. The vectors pGF2006, pGF2009 and pGF2012 are particularly suitable for this purpose.

Example 2
Methods of Screening for New Mutations.

To develop a screen for new mutants having a "short canals" phenotype a *C. elegans* strain which contains any of the above plasmids that express GFP in the excretory canal can be used. To develop a screen for new mutants with a "ventral canals" phenotype a worm strain with a stably integrated GFP-expressing plasmid is crossed with a *C. elegans* strain having the UNC phenotype, such as *C. elegans* strain MT152, unc-53 (n152) (obtained from Dr. Bob Horvitz MIT, Cambridge Mass., USA). F2 worms with short canals (UNC phenotype) are used for further screening.

General Protocol for Mutagenesis

A few thousand adult worms of the desired genetic background are treated with a hypochlorite solution to get a synchronised culture. This culture is then mutagenized using the EMS technique when the worms have reached the L4 stage (protocol for mutagenesis is as described in "Methods in Cell Biology, Vol 48 page 31–35"). As an alternative to EMS the UV-TMP technique can be used. In this method the worms are contacted with tri-methyl-psoralen and then treated with UV radiation, as described in Methods in Cell Biology, Vol 48. *Caenorhabditis elegans*: Modern biological analysis of an organism. Eds H. F. Epstein and D. C. Shakes, Academic Press. F2 worms are analysed for aberrant excretory canal phenotypes, which can easily be visualised due to the expression of GFP.

Observations of excretory canal morphology are made for two subsequent generations following contact with mutagen. Dependent on the starting genetic background of the worms, the following defects can be observed in the progeny: nematodes having shorter or longer canals, nematodes having curved or extra branched canals, nematodes having ventral or dorsal canals, nematodes having more less than two canals, nematodes having wrongly branched canals, nematodes having vacuoles or cysts, nematodes with unusual features in the excretory canal.

Example 3
A Method of Detecting Compounds that Influence the Excretory Canal Phenotype Worms stably expressing GFP in the excretory canal can be used to detect and isolate compounds that have effects on the morphology of the excretory canal as follows:

Standard agar plates for use with *C. elegans* are seeded with *E. coli* and left to full growth. Serial dilutions of compound to be tested are then pipetted onto the *E. coil* lawn and allowed to diffuse into the lawn. One transgenic *C. elegans* expressing GFP in the excretory canal (L4 stage) per dilution of compound is put onto the bacterial lawn. The plates are incubated at 21° C. and visually screened for excretory canal morphology at various time intervals and for two generations to detect aberrant phenotypes. The following defects in excretory canal morphology can be observed; nematodes having shorter or longer canals, nematodes having curved or extra branched canals, nematodes having ventral or dorsal canals, nematodes having more or less than two canals, nematodes having wrongly branched canals, nematodes having vacuoles or cysts, nematodes with unusual features in the excretory canal.

Example 4
Use of the UL6 Minimal Promoter Fragment in Expression of a Heterologous DNA in the Excretory Canal The above-described plasmids pGF2002, pGF2003, pGF2006, pGF2008, pGF2009 and pGF2012 have all been used to express GFP in the excretory cell and excretory canal of C. elegans.

The same plasmids can be used to drive the transcription of other DNA fragments than the GFP encoding fragment by simply replacing this GFP encoding fragment with any other DNA fragment of interest. Preferentially the vectors pGF2006, pGF2009 or pGF20012 are used for this purpose. As an alternative, any of the isolated and analysed promoter fragments described above and shown in SEQ ID NOs:2 to 7 can be cloned upstream of the target DNA of interest in an expression vector suitable for use in C. elegans.

Example 5

Compound Screening Assay

The following method may be used to determine whether a compound is a modulator of growth cone steering, cell shape, cell motility, tumor formation, tumor vascularisation, tumor metastasis, renal development, a pathway involved in kidney disease, development of the excretory canal, cytoskeletal organisation or surface to cytoskeleton signalling:

Standard agar plates for use with C. elegans are seeded with E. coli and left to full growth. Serial dilutions of compound to be tested are then pipetted onto the E. coli lawn and allowed to diffuse into the lawn. One transgenic C. elegans (L4 stage) per dilution of compound is put onto the bacterial lawn. The transgenic C. elegans is one expressing both a protein involved in the regulation of growth cone steering, cell shape, cell motility, tumor formation, tumor vascularisation, tumor metastasis, renal development, a pathway involved in kidney disease, development of the excretory canal, cytoskeletal organisation or surface to cytoskeleton signalling and GFP in the excretory canal. The plates are incubated at 21° C. and visually screened for excretory canal morphology at various time intervals and for two generations to detect aberrant phenotypes.

The following abnormal excretory canal morphologies can be observed; nematodes having shorter or longer canals, nematodes having curved or extra branched canals, nematodes having ventral or dorsal canals, nematodes having more or less than two canals, nematodes having wrongly branched canals nematodes having vacuoles or cysts, nematodes with unusual features in the excretory canal.

Example 6

Construction of a C. elegans Strain Stably Expressing a Reporter Gene in the Excretory Canal Although expression of reporter genes in the excretory canal from extrachromosomal arrays is sufficient to perform most applications, stable expression in C. elegans by integration would facilitate and improve most if not all the applications. Several C. elegans strains have been constructed, wherein the DNA encoding for the promoter (here designated as UL6) that drives the expression of the reporter gene, in this case GFP, is integrated the in the genome.

Method

A general method to integrate extrachromosomal DNA in to the genome of C. elegans has been described by Mello and Fire in Methods in Cell biology, Volume 48, Caenorhabditis elegans: Modem biological analysis of an organism, Chapter 19, 466–468. Here the construction of a particular example is described in detail:

A wild type N2 C. elegans strain was injected with pGF2006 (100 ng/μl) and with pUC18DNA (100 ng/μl) using standard methods, resulting in strain UG489 bgEx176. Although a relatively high transmission efficiency (up to 55%) was observed, which troubles later selections, a clean expression of GFP was observed in the excretory cell and the excretory canal.

9 cm NGM plates with a population of late stage L4 worms were gamma-irradiated for 1 hour in order to obtain a total intensity of 30 gray. 6×35 animals were isolated after irradiation, incubated for 24 hours at 20° C. and then transferred to fresh plates and further incubated at 25° C. 2×500 F1 animals were isolated after 48 hours and after 72 hours respectively, and further incubated at 25° C. 2–4 F2's per F1 were isolated and incubated at 15° C.

The progeny of these F2's was checked by selecting for plates with 75% or 100% of the progeny expressing GFP. Of these positive plates, 4 F3's were isolated and further incubated at 15° C. Again the progeny was checked for the presence of 75% to 100% of the worms expressing GFP.

The resulting integrated lines were crossed out several times to confirm that no major translocations or unlinked mutations have occurred as a result of the radiation treatment. This was done by mating wild-type C. elegans (N2) males with the hermaphrodites carrying the integration (the N2 strain can be obtained from CGC, University of Minnesota, USA). F1 males are used to cross to the mapping strains and to cross back to N2 hermaphrodites (crossing out once every generation by always using GFP male progeny, except if the site of the integration is on X).

The integrations were mapped to the C. elegans chromosomes, by applying standard techniques well known in the art. Mapping was performed using at least following strains: MSI dpy-5(e61)I;unc-4(e120)II; lon-1(e185)III and MT464 unc-5(e53)IV; dpy-11(e224)V; lon-2(e678)X.

Results

Of a total of 1000 F1 worms primary isolated, 650 lines were further examined. Out of these examined lines, eight integrated lines were retained, crossed out and mapped:

UG703 bgIs309 has strong hypodermal GFP expression, integrated on X;

UG704 bgIs310 has low hypodermal GFP expression, integrated on X;

UG705 bgIs311 has nearly no hypodermal GFP expression, integrated on X;

UG706 bgIs312 has nearly no hypodermal GFP expression, integrated on I;

UG707 bgIs313 has strong hypodermal GFP expression, integrated on IV;

UG708 bgIs314 has nearly no hypodermal GFP expression, integrated on X;

UG709 bgIs315 has low hypodermal GFP expression, integrated on X;

UG710 bgIs316 has low hypodermal GFP expression, integrated on V.

Conclusion

Of the eight independent integrated lines obtained, at least five are of good quality (bgIs311, bgIs312, bgIs314, bgIs315 and bgIs316).

Example 7

Construction of Improved Vectors to Express Genes in the C. elegans Excretory Cell The plasmid expression vectors pGF2006 and pGF2009 for expression of the reporter gene GFP both contain a nuclear localisation signal (NLS) in fusion with the reporter gene. Expression of the fusion protein (NLS-GFP) results in the translocation of a part of the total amount of the protein expressed to the nucleus of the excretory cell. Although the expression of the fusion protein is high enough to visualise the fusion protein in the whole excretory cell including the excretory canal, the present inventors decided to delete this NLS part. Expression from the UL6 promoter would hence no more result in translocation in the nucleus of the expressed gene, and provide for a more equal localisation of the expressed gene.

To test this hypothesis the NLS signal was deleted from the plasmids pGF2006 and pG2009. This was easily done by deletion of a KpnI restriction fragment resulting in the plasmids pGF2013 and pGF2014 respectively.

Equivalents

Those skilled in the art will recognize, or be able to ascertain using no more than routine experimentation, many equivalents to the specific embodiments of the invention described herein. Such equivalents are intended to be encompassed by the following claims.

All references disclosed herein (e.g., published patents, patent applications and scientific publications) are incorporated by reference in their entirety.

What is claimed is presented below and is followed by a sequence listing:

We claim:

1. A transgenic *C. elegans* containing a transgene comprising a promoter fragment which directs tissue-specific gene expression in an excretory cell of *C. elegans* operatively linked to a protien-encoding DNA fragment, wherein the promoter fragment is a nucleotide sequence selected from the group consisting of SEQ ID NO:2, SEQ ID NO:3, SEQ ID NO:4, SEQ ID NO:5, SEQ ID NO:6, and SEQ ID NO:7.

2. A transgenic *C. elegans* as claimed in claim 1, wherein the protein-encoding DNA fragment comprises a reporter gene encoding green fluorescent protein, β-galactosidase, β-lactamase, luciferase, acetohydroxyacid synthase, alkaline phosphatase, β-glucuronidase, chloramphenicol acetyltransferase, horseradish peroxidase, nopaline synthase or octapine synthase.

3. A transgenic *C. elegans* as claimed in any one of claims 1 or 2, wherein said transgene is stably integrated into a chromosome of the *C. elegans*.

4. A transgenic *C. elegans* as claimed in claim 1, further comprising a second transgene, said second transgene comprising a promoter fragment selected from the group consisting of SEQ ID NO:2, SEQ ID NO:3, SEQ ID NO:4, SEQ ID NO:5, SEQ ID NO:6, and SEQ ID NO:7, which directs tissue-specific gene expression in an excretory cell of *C. elegans* operatively linked to a protein-encoding DNA fragment.

5. A transgenic *C. elegans* as claimed in claim 4, wherein the protein-encoding DNA fragment of the second transgene comprises a reporter gene encoding green fluorescent protein, β-galactosidase, β-lactamase, luciferase, acetohydroxyacid synthase, alkaline phosphatase, β-glucuronidase, chloramphenicol acetyltransferase, horseradish peroxidase, nopaline synthase or octapine synthase.

6. A transgenic *C. elegans* as claimed in any one of claims 4 or 5, wherein one or both of the transgenes is integrated into a chromosome of the *C. elegans*.

7. A method of identifying a mutation or mutations in a gene involved in the development of the excretory canal of *C. elegans*, comprising:

(a) contacting a transgenic *C. elegans* with a mutagen, (b) identifying a mutant transgenic *C. elegans* with an altered excretory canal phenotype, and (c) identifying a mutation, or mutations, present in a gene involved in the development of the excretory canal of the mutant transgenic *C. elegans* of step (b), wherein the transgenic *C. elegans* comprises a promoter fragment selected from the group consisting of SEQ ID NO:2, SEQ ID NO:3, SEQ ID NO:4, SEQ ID NO:5, SEQ ID NO:6, and SEQ ID NO:7, in the absence of any other sequence of consecutive nucleotides from the *C. elegans* genome, operatively linked to a reporter gene.

8. A method as claimed in claim 7, wherein the mutagen is Ethyl Methyl Sulphonate, UltraViolet-TriMethylPsoralen, or X-rays.

9. A method as claimed in any one of claims 7 or 8, wherein the transgenic *C. elegans* has a wild-type genetic background or a selected mutant genetic background.

10. A method as claimed in any one of claims 7 or 8, wherein the reporter gene encodes green fluorescent protein, β-galactosidase, β-lactamase, luciferase, acetohydroxyacid synthase, alkaline phosphatase, β-glucuronidase chloramphenicol acetyltransferase, horseradish peroxidase, nopaline synthase or octapine synthase.

11. A method of determining whether a compound is modulator of the development of the excretory canal of *C. elegans*, comprising:

(a) contacting a transgenic *C. elegans* with a candidate compound suspected of being a modulator of the development of the excretory canal of *C. elegans*, (b) identifying a transgenic *C. elegans* which exhibits an altered excretory phenotype as a result of exposure to the candidate compound, and (c) determining whether the compound is a modulator of the development of the excretory canal of *C. elegans*, wherein the transgenic *C. elegans* comprises a promoter fragment selected from the group consisting of SEQ ID NO:2, SEQ ID NO:3, SEQ ID NO:4, SEQ ID NO:5, SEQ ID NO:6, and SEQ ID NO:7, in the absence of any other sequence of consecutive nucleotides from the *C. elegans* genome, operatively linked to a reporter gene.

12. A method as claimed in claim 11, wherein the transgenic *C. elegans* has a wild-type genetic background or a selected mutant genetic background.

13. A method as claimed in any one of claims 11 or 12, wherein the reporter gene encodes green fluorescent protein, β-galactosidase, β-lactamase, luciferase, acetohydroxyacid synthase alkaline phosphatase, β-glucuronidase, chloramphenicol acetyltransferase, horseradish peroxidase, nopaline synthase or octapine synthase.

* * * * *

UNITED STATES PATENT AND TRADEMARK OFFICE
CERTIFICATE OF CORRECTION

PATENT NO. : 6,465,715 B1
DATED : October 15, 2002
INVENTOR(S) : Zwaal et al.

It is certified that error appears in the above-identified patent and that said Letters Patent is hereby corrected as shown below:

Column 57,
Line 24, replace "protien" with -- protein --

Signed and Sealed this

Twelfth Day of August, 2003

JAMES E. ROGAN
*Director of the United States Patent and Trademark Office*